United States Patent [19]

Issidorides et al.

[11] 4,343,942

[45] Aug. 10, 1982

[54] QUINOXALINE DERIVATIVES

[75] Inventors: Costas H. Issidorides, Lexington, Ky.; Makhluf J. Haddadin, Beirut, Lebanon

[73] Assignee: Research Corporation, New York, N.Y.

[21] Appl. No.: 883,577

[22] Filed: Dec. 9, 1969

Related U.S. Application Data

[63] Continuation-in-part of Ser. No. 691,252, Dec. 18, 1967, abandoned, which is a continuation-in-part of Ser. No. 592,729, Nov. 8, 1966, abandoned.

[30] Foreign Application Priority Data

Nov. 2, 1967 [NL] Netherlands ........................ 6714882

[51] Int. Cl.[3] ........................................ C07D 241/40

[52] U.S. Cl. .................................. 544/354; 544/345; 544/355; 544/356; 424/250

[58] Field of Search ................ 260/250; 544/353, 345, 544/354, 355, 356; 424/250

[56] References Cited

U.S. PATENT DOCUMENTS

| | | | |
|---|---|---|---|
| 3,360,391 | 5/1972 | Ley et al. | 260/250 Q |
| 3,474,097 | 10/1969 | Johnston | 260/250 R |
| 3,557,109 | 1/1971 | Ley et al. | 260/250 R |

FOREIGN PATENT DOCUMENTS

| | | | |
|---|---|---|---|
| 6504563 | 10/1965 | Netherlands | 260/250 |

*Primary Examiner*—Nicholas S. Rizzo
*Attorney, Agent, or Firm*—Dennis P. Clarke

[57] ABSTRACT

The synthesis of quinoxaline and benzimidazole-N-oxides and of ester and amide derivatives of 3-hydroxy-2-quinoxalinecarboxylic acid by a novel process consisting of the reaction between a benzofuroxan and an activated methylene-containing compound under basic conditions.

17 Claims, No Drawings

QUINOXALINE DERIVATIVES

CROSS-REFERENCE TO RELATED APPLICATIONS

This application is a continuation-in-part of copending application Ser. No. 691,252, filed Dec. 18, 1967, which in turn is a continuation-in-part of copending application Ser. No. 592,729, filed Nov. 8, 1966, both now abandoned.

BACKGROUND OF THE INVENTION

This invention relates to a novel synthetic procedure and, more particularly, to a novel method for the preparation of quinoxaline-di-N-oxides and related compounds such as benzimidazole-di-N-oxides and 1-hydroxybenzimidazole-3-oxides.

The compounds prepared by the novel subject process are useful in the control of various pathogenic microorganisms. Also, as shown in U.S. Pat. No. 3,047,579, such oxides are generally prepared by processes involving the direct oxidation of quinoxaline compounds and usually require the corresponding quinoxaline compound as the starting material. Oxidation reactions are generally known to be somewhat non-selective and may give rise to low yields of the desired product together with one or more difficult to separate by-products.

Landquist et al., J. Chem. Soc. 2052 (1956) reported the preparation of the ethyl ester and the amide of 3-methyl-2-quinoxalinecarboxylic acid-di-N-oxide in a search for compounds of improved antibacterial or antiprotozoal activity. However, no utility is alleged for either of these compounds.

Netherlands Pat. No. 6,504,563, granted Oct. 18, 1965, reports the methyl ester of 2-quinoxalinecarboxylic acid-di-N-oxide and a series of N-substituted derivatives of 2-quinoxalinecarboxamide-di-N-oxide in which the substituent is an N,N-dialkylaminoalkyl group; e.g., N,N-dimethylaminoethyl-; N,N-diethylaminoethyl-; N,N-diethylaminopropyl-; N,N-dimethylaminoisobutyl-; and N,N-diethylamino-t-amyl; or a hydroxyalkyl group; e.g., 2-hydroxyethyl. The compounds are described as active agents against cancer. French Pat. No. M3717, granted Jan. 3, 1966, generically discloses 2-quinoxalinecarboxamide-di-N-oxides in which the carboxamide group may be substituted with an alkyl, substituted alkyl, aryl, cycloalkyl, aralkyl, or cycloalkylalkyl group; or may form a heterocyclic amide, e.g., a piperidide. They are reported to be of use in human therapy as antitubercular, antibacterial, anticancer, antivirus and antiprotozoal agents.

Belgian Pat. No. 697,976, granted Nov. 3, 1967, describes a variety of N-substituted derivatives of 3-methyl-2-quinoxalinecarboxamide-di-N-oxide in which the N-substituent is phenyl, substituted phenyl, dodecyl or ethyl. Also disclosed are cyclic amides, e.g., pyrrolidide and piperidide. They are said to be of value as intermediates for the preparation of vegetation protection agents and pharmaceutical agents and are prepared by the reaction of a benzofuroxan with a compound having a keto group adjacent to a methylene or methyl group in the presence of ammonia or a primary aliphatic amine.

Belgian Pat. No. 721,724, published Apr. 2, 1969, describes a variety of N-substituted 3-methyl-2-quinoxalinecarboxamide-di-N-oxides wherein the N-substituent is alkyl, hydroxyalkyl, lower alkoxyalkyl, carbalkoxyalkyl, monoalkylaminoalkyl or di(alkyl)aminoalkyl groups as antibacterial agents.

Haddadin and Issidorides (Tetrahedron Letters, No. 36, 3253–6, 1965) reported the preparation of quinoxaline-di-N-oxides by the reaction of enamines with benzofuroxan (referred to therein as isobenzofuroxan).

The gram-negative antibacterial activity of several quinoxaline-di-N-oxides bearing 2-alkyl or 2,3-dialkyl groups has been described by Landquist et al., U.S. Pat. No. 2,626,259 issued Jan. 20, 1953, and by Wiedling, Acta Pathol et Microbiol. Scand. 22, 379–91 (1945), McIlwain, J. Chem. Soc. 322 (1943) and King et al., J. Chem. Soc. 3012 (1949), disclose the antibacterial activity of 2-methyl-3-n-amylquinoxaline-di-N-oxide and of several 6-substituted quinoxaline-di-N-oxides, respectively. Hurst et al., Brit. J. Pharmacol. 8, 297 (1953) report on the antiviral properties of quinoxaline-di-N-oxide and various derivatives thereof against the largest viruses of the psittacosis-lymphogranuloma group. Hurst et al. report that few of the products were active against the virus (lymphogranuloma) in the chick embryo.

SUMMARY OF THE INVENTION

In accordance with the present invention, a general organic synthetic method is disclosed for the preparation of quinoxaline and benzimidazole-N-oxides which comprises reacting a benzofuroxan in the presence of a base with a compound having an activated methylene group, said compound being selected from the group consisting of a first division consisting of those wherein the methylene group is linked to, i.e., activated by, two electron-withdrawing groups at least one of which contains a carbon atom alpha to the methylene group, and a second division consisting of those wherein the methylene group is linked to, i.e., activated by, one electron-withdrawing group which is nitro or a carbonyl group of a ketone or aldehyde.

The preparative reactions of the present invention may be exemplified as follows:

I

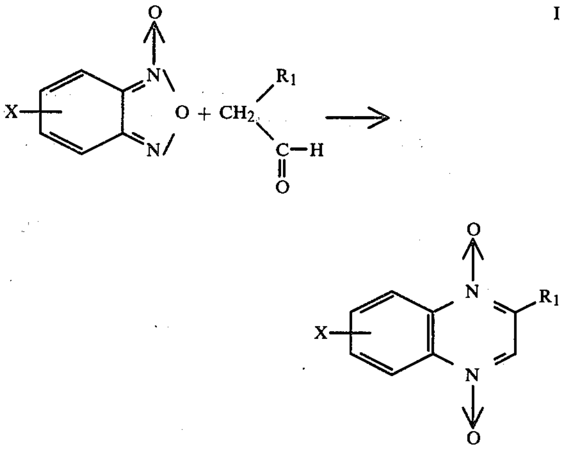

where the activated methylene containing compound is a hydrocarbyl aldehyde; where $R_1$ may, for example, be hydrogen, alkyl and preferably alkyl of up to 6 carbon atoms, substituted alkyl, alkenyl and substituted alkenyl, aryl, e.g., phenyl, or substituted aryl. Substituents ($R_3$) on $R_1$ take many forms, e.g., halogen, hydroxyl; alkoxyl; acetoxyl; alkyl; aryl; acetal; amino; substituted amino such as alkylamino, arylamino, acylamino or aroylamino; and electron-withdrawing groups such as carboxy, carbalkoxy, nitrile and amide, in this case not linked directly to the methylene group.

IIA

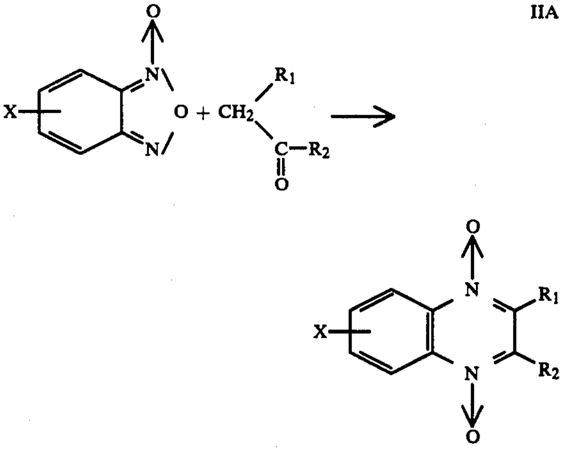

where the activated methylene containing compound is a non-cyclic hydrocarbyl ketone; where $R_2$ is not hydrogen in this case but otherwise is illustrated by the range of $R_1$ values listed in I above.

IIB

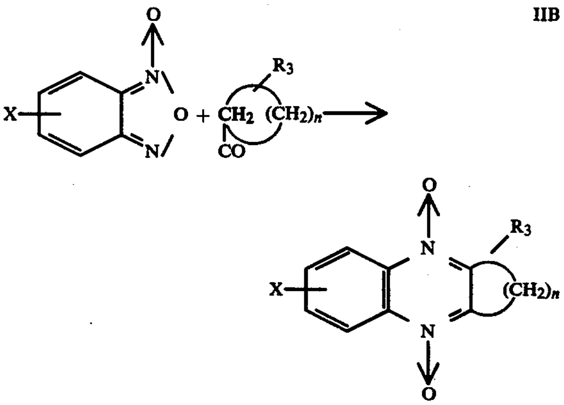

where the $R_1$ and $R_2$ of IIA are here taken together to form an alicyclic ring in which n=2-16, which ring may be substituted with substituent $R_3$ such as those described in I.

IIC

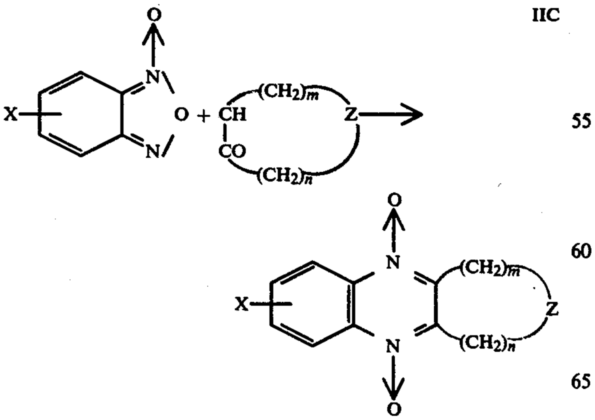

(plus the isomeric compound in which n=n−1)

where the carbonyl group and the adjacent methylene group form part of a heterocyclic ring, e.g., a heterocyclic ketone, where m=0 or 1 and n=2 or 3. The hetero atom Z can be oxygen, sulfur, imino (NH) or substituted imino, wherein the substituent on the nitrogen may, for example, be alkyl, aryl, such as phenyl, acyl such as acetyl or aroyl. As in IIB, the ring may be substituted by substituent $R_3$.

IIIA

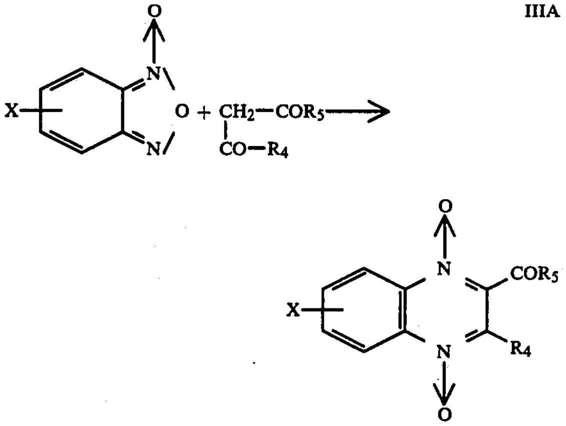

where $R_4$ or $R_5$ may be hydrogen and either or both may be alkyl groups, e.g., of 1 to 6 carbon atoms, substituted alkyl or aryl groups. Appropriate substituents for $R_4$ and $R_5$ are as exemplified in I under the definition of $R_3$.

IIIB

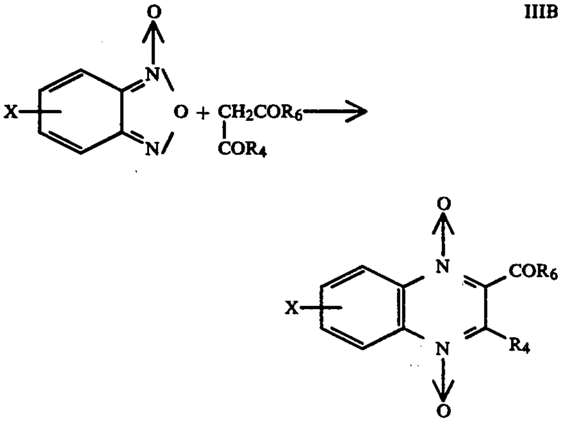

where $R_4$ is as exemplified as in IIIA and $R_6$ may be $OR_7$, e.g., where $R_7$ is alkyl, aryl or alkaryl; or $NR_8R_9$ where $R_8$ and $R_9$ may be substituents such as hydrogen, alkyl or aryl, e.g., phenyl.

IIIC

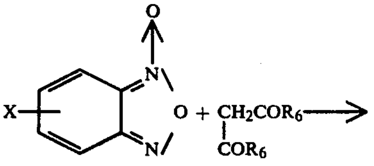

-continued

Reduced product and/or

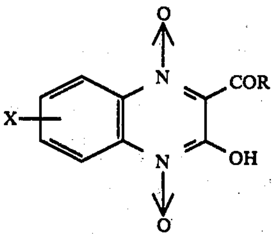

where $R_6$, for example, is $OR_7$ or $NR_8R_9$, where $R_7$, $R_8$ and $R_9$ are as exemplified in IIIB.

IIID

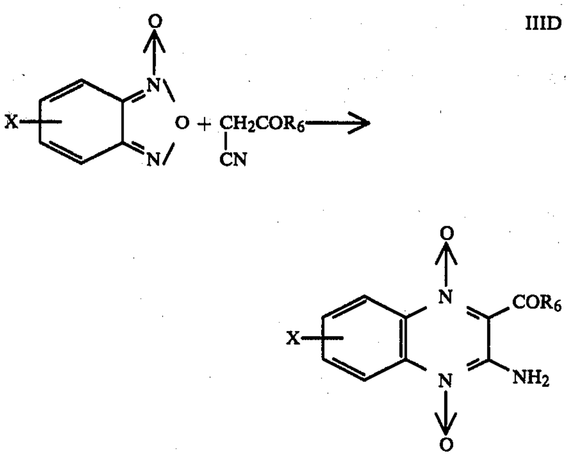

where $R_6$ is exemplified as in IIIC.

IIIE

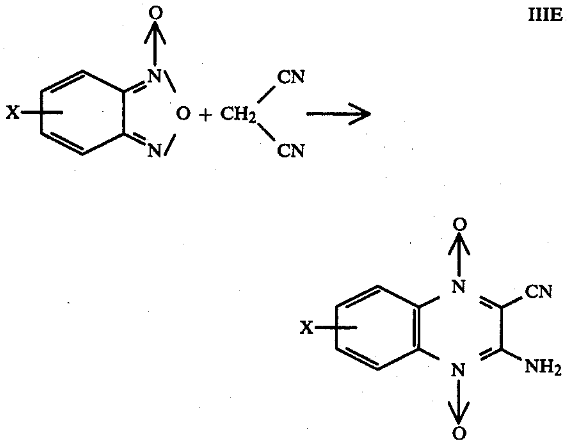

IVA

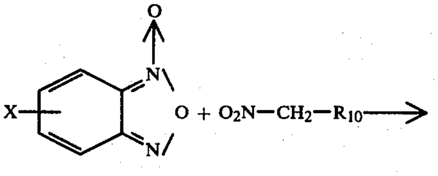

-continued

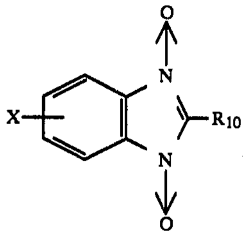

where $R_{10}$ is hydrogen, alkyl, substituted alkyl, aryl, substituted aryl, carbalkoxy, carboxamido, or the like.

IVB

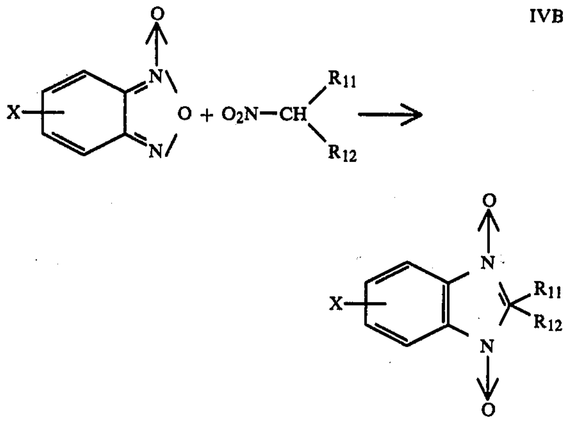

where $R_{11}$ and $R_{12}$ are not hydrogen in this case, but otherwise as exemplified as $R_{10}$ in IVA, or taken together may form a carbocyclic ring or substituted carbocyclic ring, with substituents as previously described.

Reaction sequences I through IIIE above concern the reaction between a benzofuroxan with a methylene-containing compound activated by one or two electron-withdrawing groups to provide a quinoxaline-di-N-oxide. Reaction sequences IVA and IVB above deal with the reaction between a benzofuroxan with primary and secondary nitro compounds. As is evident, the primary nitro compounds yield hydroxy benzimidazole-N-oxides (IVA) whereas the secondary derivatives provide the benzimidazole-di-N-oxides (IVB).

The substituents, of which there can be from one to four, on the fused aryl moiety of the benzofuroxan and the resulting quinoxaline-di-N-oxide or benzimidazole compound, can vary widely. For example, at least one of the following substituents can be present: hydrogen, lower alkyl, lower alkoxy, chloro, bromo, fluoro, trifluoromethyl, di(lower alkyl)amino, amino, carboxy, carbamyl, carbo(lower alkoxy), lower alkylmercapto, lower alkylsulfoxy, lower alkylsulfonyl, sulfonamido, N-(lower alkyl)sulfonamido and N,N-di(lower alkyl)-sulfonamido. The favored positions on the aryl ring of the benzofuroxan are the 5- and/or 6-positions (see formula II). Of special interest for these positions are at least one of the following substituents: hydrogen, methyl, chloro, fluoro, trifluoromethyl, methoxy and sulfonamido. A single substituent, that is, a 5- or 6-substituent, is usually favored over a 5,6-disubstituted derivative for reasons of economy as regards the benzofuroxan reactant. Hence, the reason for illustration of a single "X" substituent in the above formulae. Nitro, hydroxy and mercapto groups are not desirable substituents since they retard the reaction and/or give undesired products and poor yields.

The locations of the substituents $X_1$, $X_2$, $X_3$, and $X_4$ illustrated herein is somewhat arbitrary since the exact points of attachment of the methylene containing compound with the benzofuroxan are not known. For example, if one reacts a benzofuroxan of the formula

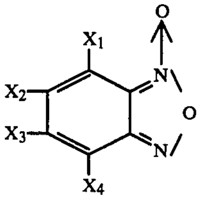

with a reactant $R_1$—$CH_2$—$COR_2$, two products are possible as shown by the formulae below:

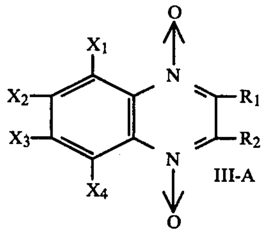

III-A

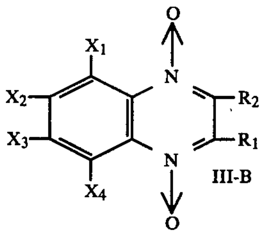

III-B

In formula III-A, the variables $X_1$, $X_2$, $X_3$ and $X_4$ are attached to the 5,6,7, and 8-positions whereas in III-B, they are attached to the 8,7,6,5-positions of the quinoxaline-di-N-oxide product. The examples herein use the first system of nomenclature. It must be remembered throughout that this designation is purely arbitrary except in the case where $X_1=X_4$ and $X_2=X_3$, and in the case wherein all four variables are alike.

Thus, benzofuroxan or a substituted benzofuroxan can be used in the process of this invention. Such benzofuroxans are readily available or easily prepared by those skilled in the art. For instance, the preparation of various substituted benzofuroxans is described by Kaufman et al. in Chem. Rev. 59, 448 (1959) in an article entitled "The Furoxans."

The methylene-containing reagent in reaction sequences I through IIIE can be either singly or doubly activated by electron-withdrawing groups. In the case where it is activated by one electron-withdrawing group, the molecule will be either a ketone which is aliphatic or alicyclic, substituted or unsubstituted, or an aldehyde, substituted or unsubstituted. It must be kept in mind throughout that the subject process is a very basic one. Hence, when reference is made to such general terms as aldehydes and ketones, it is meant to include any and all ketones and aldehydes. In addition to substitution, there may be unsaturation in the carbon chain.

Regarding said ketone and aldehyde reactants, it is found that the examples encompassed by the following general structures are preferred:

V  VI 

wherein R is alkyl of up to 4 carbon atoms which may be alike or different and in the case of said ketone, one of said R groups may contain an —OH group thereon.

This characteristic of being a basic synthetic method applies equally when the methylene-containing compound is activated by two electron-withdrawing groups. In fact, the only restriction on such a reagent is that one of said electron-withdrawing groups must have a carbon atom alpha to said methylene group. The methylene group, as is evident from the illustrations herein, becomes part of the resulting six-membered di-N-oxide ring. For instance, one of said two electron-withdrawing groups may be alkylsulfonyl or aminosulfonyl in combination with any other electron-withdrawing group which is capable of providing the second part necessary for formation of the six-membered ring. Therefore, when said methylene-containing compound is doubly activated, any electron-withdrawing group will be found to be satisfactory. Numerous reactants will occur to one skilled in the art: typical examples include β-ketoesters, β-diketones, malonic acid esters, malononitrile and combinations thereof such as nitrile-esters, β-ketoamides, ester-amides, cyanoamides, ketosulfonyl compounds, ketosulfonamides, and so forth.

The preferred β-diketones, β-ketoesters and malonic esters have the following general formulae, respectively:

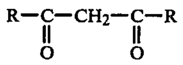 VII

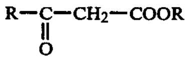 VIII

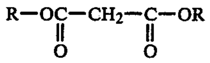 IX wherein the R groups represent alkyl groups containing from 1 to 4 carbon atoms which may be alike or different.

In the preparation of these quinoxaline-di-N-oxides, particularly with the malonate reactants, a proportion of the corresponding quinoxaline compound is formed along with the quinoxaline-di-N-oxide. The compound of reduced form may be separated by conventional separation techniques, e.g., filtration of the reaction mixture, followed by recovery of the quinoxaline-di-N-oxide from the filtrate. With malonamates, that is, half-ester, half-amide derivatives of malonic acid, the quinoxaline compound appears to be the predominant product.

DETAILED DESCRIPTION OF THE INVENTION

Reaction sequences IVA and B above described the reaction between a benzofuroxan with a nitro compound as indicated. If the nitro compound is of the primary type, that is, where there is a $CH_2$ group alpha to the nitro group, then the resulting product is a 1-hydroxy-3-oxide illustrated by reaction IVA. Alternatively, if the nitro compound is of the secondary type, that is, where the adjacent methylene has only one hydrogen attached, the resulting product is a benzimidazole-1,3-di-N-oxide. This is the only instance herein where the term "methylene" does not contain 2 hydrogen atoms. Although the mechanisms involved in reaction sequences I through IIIE and IVA through IVB are similar, in the latter there is a marked difference in the type of products obtained. As is evident, the quinoxaline-di-N-oxides contain a six-membered B ring whereas the benzimidazoles contain a five-membered B ring. Once again, in keeping with the finding that the herein disclosed process is indeed a basic one, the term nitro compounds includes any and all such derivatives. With regard to the organo nitro reactant, compounds encompassed by the following general structure are preferred for the process of this invention:

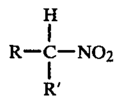

X wherein R is alkyl of up to 4 carbon atoms, and R' is H or alkyl of up to 4 carbon atoms.

Concerning all the herein described methylene-activated reagents, it should be noted that most of them are available on a commercial basis but if such is not the case, they can be prepared by well-known synthetic organic techniques outlined in most basic organic textbooks.

As a necessary element of the herein disclosed novel process, the reaction sequences described above (I through IVB) must be effected in the presence of a base. Such a base is of varied character. For instance, it is meant to contemplate such bases as organic amines, ammonia, alkali metal hydroxides, hydrides and alkoxides. Representative of such bases are ammonia, primary amines such as n-propylamine, n-butylamine, aniline, cyclohexylamine, benzylamine, p-toluidine, ethylamine, octylamine; secondary amines such as diethylamine, dipropylamine, methyl-n-butylamine, pyrrolidine, morpholine, piperidine, pyrrole, pyrroline, N-methylaniline, N-methylbenzylamine, pyrimidine; tertiary amines such as triethylamine, trimethylamine, N,N-dimethylaniline, N-methylpyrrolidine, N,N-dimethylpyrimidine, N-methylmorpholine, and 1,5-diazabicyclo[4,3,0]-5-nonene; sodium hydroxide, potassium hydroxide, ammonium hydroxide, sodium ethoxide, potassium methoxide, and sodium hydride.

Once again, since the herein disclosed novel process is a basic one, the term base is typified by the above illustrated examples. However, there is no need to be restricted to this group. Furthermore, it has been found that it is more preferable to use certain bases for each of the possible methylene-containing compound reagents. For instance, it is found that when said methylene-containing compound is a ketone, that the preferred base to use is an organic amine or ammonia. Similarly, for aldehydes, β-ketoamides and the nitro compounds, the same bases are preferred. When said activated methylene-containing compound is a β-diketone or a β-ketoester, the preferred bases are inorganic amines, alkali metal hydroxides and alkali metal alkoxides. When the reagent is a malonic ester, the preferred base is an alkali metal alkoxide. In the last two instances, it is desirable that the alkyl group of the alkali metal alkoxide be the same as the alkyl group of the ester to avoid ester interchange.

The amount of base used in any of the reactions discussed herein is not critical but can vary widely, e.g., from a trace or catalytic amount of base, that is, from about 0.001 percent by weight, based on the benzofuroxan reactant present, to even molar excess amounts as occurs when the base is used as solvent. In general, optimum amounts range from about 0.1 percent by weight to about equimolar amounts based on the benzofuroxan used. As will be readily appreciated, the optimum proportion of base will vary with the nature of the particular reactants employed, as well as specific reaction conditions. Accordingly, the optimum proportion of base is most conveniently established by routine experimentation using small scale laboratory reactions.

The inclusion of a solvent in the basic process of this invention is not critical and its desirability will depend on many factors, e.g., the consistency of the reaction mixture, the temperature desired, the ease of maintaining a given temperature.

If the reactants when combined produce a viscous system or if temperature control is difficult, it is highly desirable to include an appropriate solvent. For purposes of this invention, an appropriate solvent is any solvent which does not react in an undesired way with either the reactants or the final products. By choosing the appropriate solvent, better temperature control is possible since specific elevated reaction temperatures can be attained by selecting a solvent having the desired boiling point. Suitable solvents are aromatic hydrocarbons such as benzene, toluene, xylene; acetonitrile, N,N-dimethylformamide, halogenated hydrocarbons such as methylene chloride, chloroform, carbon tetrachloride; alcohols such as methanol, ethanol, propanol, n-butanol; ethers such as diethyl ether, dioxane, tetrahydrofuran; ethylene glycol and ethers of ethylene and diethylene glycol. Additionally, an excess of the base can be used as solvent provided, of course, it is liquid at the reaction temperature employed. This provision, as those skilled in the art will recognize, limits the use of bases as solvents to organic amines. In such instances, the base is present in great excess relative to the benzofuroxan reactant.

Reaction temperatures do not appear to be critical in the present process although it is generally preferred to carry out the reaction at temperatures above room temperature. A preferred range is from about 30° C. to about 100° C. Temperatures below 30° C. may be employed, for instance, 0° C. to 30° C., but are less preferred because of the relative slowness of the reaction and generally poorer yields.

The time required for the reaction will vary considerably with the nature of the reactants, the base used, and the temperature. Reaction periods ranging from about 15 minutes to about 30 hours give substantial yields of the desired products. Higher temperatures, as expected, require shorter reaction periods than do lower temperatures for a given set of reactants. In general, reaction periods of from about 15 minutes to about 12 hours are adequate.

The molar ratio of reactants, that is, of the benzofuroxan and the methylene-activated reactant, is not critical but can vary widely, e.g., from equimolar proportions to a large excess of either reactant. They are, in general, reacted in equimolar proportions. As a practical measure when using a readily available methylene-activated reactant, e.g., acetone, a large excess of the reagent is used to ensure as complete a conversion of the benzofuroxan to the desired product as is possible. Further, the excess methylene-activated reactant can also serve as solvent.

The order of addition of reactants is not critical to the success of this process. They can be added all at once along with the base or the base can be added to a mixture of the benzofuroxan and methylene-activated reactant. This latter method is advantageous in the case of exothermic reactions since it facilitates temperature control apparently by regulating the rate of reaction. In the case of such exothermic reactions, the use of an appropriate solvent also contributes to temperature control. As alternatives to the above methods of addition of reactants, either reactant can be added to the other in the presence of the proper base, or the reactants can be added simultaneously to the base.

When benzofuroxan reacts with a symmetrical β-diketone (formula VII) there is no question as to the structure of the product involved since the steric effects of the R groups are identical. However, when unsymmetrical β-diketones (formula VII, R groups are not alike) react with benzofuroxan, a single product or isomeric products are possible, depending upon the steric effects of the R groups. A series of reactions with 1-benzoyl-2-alkanones ($C_6H_5$—CO—$CH_2$—CO—R wherein R is methyl, ethyl, i-propyl and t-butyl) as the methylene-activated reactants clearly demonstrate the steric effects of the R group. When reacted with benzofuroxan in the presence of triethylamine or diethylamine as base, the first two members of the series produced only 2-R-3-benzoylquinoxaline-di-N-oxide (R=methyl, ethyl). The third member produced an isomeric mixture of 2-isopropyl-3-benzoylquinoxaline-di-N-oxide and 2-isobutyryl-3-phenylquinoxaline-di-N-oxide. The fourth member gave 2-pivalyl-3-phenylquinoxaline-di-N-oxide as the only product isolated.

A second series of reaction using p-(substituted)benzoyl acetones as the methylene-activated reactant produced a single product-2-methyl-3-p-(substituted)benzoylquinoxaline-di-N-oxide-regardless of the nature of the p-substituent.

With regard to the isolation of the desired products of this invention, it is found in many instances that in the course of or upon completion of reaction the product precipitates out in crystalline form. In such cases, all that is required is filtration, washing and drying. If, on the other hand, the product does not completely precipitate or if it remains in solution, the reaction workup consists of evaporating the mixture almost to dryness and then filtering the product. If the sodium salt of the product forms, as it does in certain instances, the general procedure consists of filtering said salt, dissolving it in water, acidifying the solution and subsequently filtering the product which forms. All of the above techniques are well known to those skilled in the art.

Chemical and physical evidence confirms the di-N-oxide structure of products obtained from reaction scheme I. For example, the infrared spectrum of the product of the reaction of dibenzoylmethane and benzofuroxan, assigned the structure 2-phenyl-3-benzoylquinoxaline-di-N-oxide, displayed strong bands at $cm^{-1}$ 1670 (conjugated carbonyl), 1335 (N-oxide), 770 (orthosubstituted phenyl) and 690 (monosubstituted phenyl). Reduction with sodium dithionite gave a product identical (mixed melting point and infrared spectrum) with a sample of 2-phenyl-3-benzoylquinoxaline prepared according to the method of Brandt et al. Ann. 688, 189 (1965).

The product from benzofuroxan and acetylacetone was assigned the structure 2-methyl-3-acetylquinoxaline-di-N-oxide. Its infrared spectrum showed intense bands at $cm^{-1}$ 1700 (carbonyl), 1330 (N-oxide), and 770 (ortho-substituted phenyl). These data are consistent with the assigned structure.

The verification that the herein disclosed compounds are effective antimicrobial agents is established by experimental evaluations. One such in vivo evaluation consists of seeding nutrient broth containing various concentrations of the subject compounds with a particular organism and subsequently determining the "minimum inhibitory concentration" (MIC). The MIC is defined as the minimum concentration of the antimicrobial test compound (in micrograms/milliliter) at which growth of the microorganism failed to occur. For instance, the following is only a representative list of compounds disclosed herein which have exhibited in vitro activity in the above described procedure:

Quinoxaline-di-N-Oxide 2-methylquinoxaline-di-N-oxide
2-hydroxymethyl-3-methylquinoxaline-di-N-oxide
2,3-trimethylenequinoxaline-di-N-oxide
2-carbethoxymethyl-3-methylquinoxaline-di-N-oxide
1-hydroxybenzimidazole-3-oxide
2,2-dimethyl-2H-benzimidazole-1,3-dioxide
2-formyl-quinoxaline-di-N-oxide Illustrative MIC values are shown in the examples. It should be understood that these are only representative illustrations and are provided to show typical desirable results.

Since all the products of the present invention possess in vitro activity against harmful microorganisms, they are useful as industrial antimicrobials, for instance, water-treatment, slime-control, paint preservation, wood preservation, and so forth, as well as for topical application purposes, for example, disinfectants, and so forth. In the latter application, it will often be convenient to compound the selected product with a pharmaceutically-acceptable carrier for ease in application. Thus, for example, they may be blended with vegetable or mineral oils or incorporated in emollient creams. Similarly, they may be dissolved or dispersed in liquid carriers or solvents such as water, alcohol, glycols or mixtures thereof or other reaction-inert media, that is media which have no harmful effect on the active ingredient. For such purposes, it will generally be acceptable to employ concentrations of active ingredients of from about 0.01 percent to about 10 percent by weight based on total composition.

Furthermore, many of the compounds described herein find particular utility in the growth promotion of animals in the control of chronic respiratory disease in poultry, infectious sinusitis in turkeys, and urinary tract and systemic and non-systemic infections in animals, including man.

Additionally, many of the novel compounds described herein are effective against gram-positive and-/or gram-negative bacteria in vivo. This broad spectrum activity, that is, activity against both gram-positive and gram-negative bacteria, is in contrast to the typical gram-negative activity exhibited by quinoxaline-di-N-oxides in general.

As will be obvious to those skilled in the art, many of the products described herein are valuable intermediates for the production of more highly substituted quinoxaline-di-N-oxides. For example, the products bearing a methyl substituent, e.g., 3-methyl-2-quinoxalinecarboxamide-di-N-oxide, can be brominated to the corresponding bromomethyl derivative, which can then be converted by known methods to an ether, a thioether, an amine or substituted amine, a mercapto or hydroxy group. Still further, products bearing an hydroxy or mercapto group can be converted to acyloxy, acylthio, ether or thioethers.

The following examples are provided by way of illustration.

EXAMPLE I

2-Methylquinoxaline-di-N-Oxide

A mixture containing benzofuroxan (6.8 g., 0.05 moles), acetone (20 ml.) and acetonitrile (20 ml.) is heated to reflux. Pyrrolidine (1.0 ml., 0.012 moles) is added and the resulting reaction mixture refluxed for about 15 minutes and then allowed to cool. After sitting at room temperature overnight, the product which precipitates is filtered, washed and dried to give a 68 percent yield, M.P. 172°-174° C. (MIC against Past. Multocida in 50 mcg./ml.)

EXAMPLE II

2,3-Dimethylquinoxaline-di-N-Oxide

The procedure of Example I is repeated to prepare this product wherein methylethyl ketone and morpholine are used in stoichiometric equivalent amounts, in place of acetone and pyrrolidine, respectively, and similar results are obtained. The product is recrystallized from a chloroform-hexane (1:1) mixture, M.P. 190°-192° C.

EXAMPLE III

2-Ethyl-3-Methylquinoxaline-di-N-Oxide

The procedure of Example I is repeated to prepare this product wherein 3-pentanone and morpholine are used, in stoichiometric equivalent amounts, in place of acetone and pyrrolidine, respectively, and similar results are obtained. The product is recrystallized from a chloroformhexane (1:1) mixture, M.P. 143°-146° C.

The procedures of Examples I through III are repeated wherein $NH_3$ gas is used in lieu of the bases indicated (morpholine, pyrrolidine) with comparable results. The reagents are combined and $NH_3$ gas is bubbled into the mixture through a dispersion tube for 5 minutes whereupon the resulting reaction mixture is then treated as indicated.

EXAMPLE IV

The procedure of Example I is repeated to prepare the following products wherein the listed reagents (ketone, base) are used in place of acetone and pyrrolidine, in stoichiometric equivalent amounts, to yield substantial amounts of products shown.

| Ketone | Base | Product |
|---|---|---|
| heptanone-4 | morpholine | 2-ethyl-3-propylquinoxaline-di-N-oxide |
| hexanone-2 | morpholine | 2-methyl-3-propylquinoxaline-di-N-oxide |

EXAMPLE V

A mixture containing benzofuroxan (6.8 g., 0.05 moles), cyclohexanone (5.9 g., 0.06 moles), morpholine (4.3 g.) and benzene (300 ml.) is refluxed for two hours, allowed to cool and then evaporated almost to dryness. The solid material (product) is triturated with an acetone-ether (1:1) mixture and then filtered to give 5.0 g. of product, M.P. 158°-168° C. dec. Recrystallization from benzene gives product, M.P. 170°-175° C. dec. (MIC against Strep. pyogenes is 6.25 mcg./ml.)

EXAMPLE VI

The procedure of Example V is repeated to prepare the subject product wherein a stoichiometric equivalent amount of cyclobutanone is used in lieu of cyclohexanone and comparable results are obtained. Recrystallization from a chloroform-hexane (1:1) mixture gives a product M.P. 213.5°-214.5° C. dec.

Analysis: Calc'd. for $C_{10}H_8O_2N_2$: %C, 63.82; %H, 4.28; %N, 14.89. Found: %C, 63.85; %H, 4.29; %N, 14.86.

EXAMPLE VII

2,3-Trimethylenequinoxaline-di-N-Oxide

The procedure of Example V is repeated to prepare the above product wherein a stoichiometric equivalent amount of cyclopentanone is used in place of cyclohexanone with comparable results. The product is recrystallized from a chloroform-hexane (1:1) mixture, M.P. 174°-177° C.

EXAMPLE VIII

The procedure of Example V is repeated to prepare the products derived from the list of cyclic ketones shown below wherein a stoichiometric equivalent amount of each of said cyclic ketones is used in place of cyclohexane and a stoichiometric equivalent amount of the amine shown is used in place of morpholine with comparable results.

| Ketone | Amine | Melting Point |
|---|---|---|
| α-methylcyclohexanone | morpholine | 138-140° C. |
| cyclododecanone | morpholine | 139.5-142° C. |
| cyclopentadecanone | morpholine | — |
| norcamphor | pyrrolidine | 202-203° C. |

EXAMPLE IX

2-Hydroxymethyl-3-Methylquinoxaline-di-N-Oxide

A. A mixture of benzofuroxan (0.1 moles), 4-hydroxy-2-butanone (0.15 moles), pyrrolidine (0.025 moles) and dimethylformamide (20 ml.) is stirred at room temperature for about 2 to 3 hours. The solid which precipitates is filtered off, washed with acetonitrile and dried to provide 11 g. (54 percent) of product, M.P. 180°-183° C.

B. A solution of benzofuroxan (13.61 g., 0.1 mole) and 4-hydroxy-2-butanone (8.81 g., 0.1 mole) in 100 ml. methanol is treated with ammonia gas, introduced through a dispersion tube for 10 minutes. This leads to a temperature rise which does not exceed 50° C. After about 40 minutes the temperature has returned to about 28° C. and the reaction mixture is stored overnight at room temperature. The resulting slurry is filtered to recover a first crop of product (5.5 g., melting at 165°-168° C.). The filtrate yields a second crop (2.2 g., melting at 164°-168° C.). It is purified by recrystallization from benzene.

EXAMPLE X

2-Carbethoxymethyl-3-Methylquinoxaline-di-N-Oxide

A mixture of benzofuroxan (0.01 moles) ethyl levulinate (0.1 moles), morpholine (8.7 g.) and chloroform (50 ml.) is refluxed for about 4 hours. The resulting mixture is then evaporated almost to dryness and filtered. The solid precipitate is recrystallized from acetone-hexane (1:1) to give good yield of product, M.P. 150°-152° C.

Analysis: Calc'd. for $C_{13}H_{14}N_2O_4$: %C, 59.56; %H, 5.35; %N, 10.67. Found: %C, 59.61; %H, 5.46; %N, 10.72.

EXAMPLE XI

A. 2-Phenyl-3-Benzoylquinoxaline-di-N-Oxide

Benzofuroxan (3.4 g.) and dibenzoylmethane (5.6 g.) were dissolved in warm triethylamine (25 ml.) and allowed to stand at room temperature for twenty-four hours. The resulting yellow precipitate was thinned with triethylamine and collected by filtration. The filtrate was allowed to stand for 30 hours and a second crop of crystals collected. The total yield of 2-phenyl-3-benzoylquinoxaline-di-N-oxide was 3.6 g. or 42 percent of the theoretical. Recrystallization from methanol gave thin yellow needles melting at 234° C.

Infrared: 1670, 1335, 1250, 1090, 900, 870, 770, 690 $cm^{-1}$

Analysis: Calc'd. for $C_{21}H_{14}N_2O_3$: %C, 73.67; %H, 4.12; %N, 8.18. Found: %C, 73.88; %H, 4.06; %N, 8.36.

Melting points of most di-N-oxides vary slightly with the rate of heating and are uncorrected. Infrared spectra were run in Nujol mulls on a Perkin-Elmer Model No. 137 spectrophotometer.

B. 2-Phenyl-3-Benzoylquinoxaline

2-Phenyl-3-benzoylquinoxaline-di-N-oxide (0.5 g.) was dissolved in hot methanol (150 ml.). The solution was cooled to room temperature and concentrated hydrochloric acid added (1 ml.). A solution of sodium dithionite (1 g. in 5 ml. of warm water) was added slowly to the stirred solution. A black coloration developed and disappeared to give a colorless solution. Water was added (200 ml.) and the solution was stirred for ten minutes. The resulting yellowish solid was collected, washed with water, and recrystallized from methanol after charcoal treatment to give 0.42 g. of shiny prisms melting at 150° C.

Infrared: 1670, 1018, 925, 770, 740, 715, 700-690 $cm^{-1}$

The product was identical (mixture melting point and superimposable infrared spectra) with an authentic sample of 2-phenyl-3-benzoylquinoxaline.

C. 2-Phenylquinoxaline-di-N-Oxide

2-Phenyl-3-benzoylquinoxaline-di-N-oxide (1 g.) was suspended in 2 percent methanolic potassium hydroxide (45 ml.). The mixture was heated until the solid dissolved and then cooled with stirring. The resultant precipitate was collected and washed thoroughly with methanol. The yield was 0.65 g. of 2-phenylquinoxaline-di-N-oxide as yellow needles melting at 205°-206° C. This compound has been reported by J. K. Landquist, J. Chem. Soc., 2822 (1953).

The mother liquor was allowed to stand overnight and filtered. The filtrate was acidified with dilute hydrochloric acid and extracted with ether. The ether extract was dried and evaporated to leave 0.2 g. of benzoic acid as the residue.

EXAMPLE XII

2-Methyl-3-Acetylquinoxaline-di-N-Oxide

A. Benzofuroxan (5.4 g.) and acetylacetone (4.5 g.) were dissolved in triethylamine (10 ml.), and the solution allowed to stand at room temperature for 18 hours. The yellow precipitate was collected, washed with chilled methanol, and dried to afford 5.45 g. of product. The mother liquor, after standing overnight, gave a second crop of product. The total yield of 2-methyl-3-acetylquinoxaline-di-N-oxide melting at 152° C. was 6.88 g. or 78 percent. Recrystallization from methanol raised the melting point to 153°-154° C. (MIC against P. vulgaris is 6.25 mcg./ml.)

The n.m.r. spectrum showed singlets at 7.55 (3H) and 7.34 (3H), and multiplets centered at 2.24 (2H) and 1.52 (2H) in deuterated chloroform with TMS as internal reference set at 10 (Varian A-60 spectrometer).

Infrared: 1700, 1510, 1330, 1270, 1100, 1050, 830, 770 $cm^{-1}$

Analysis: Calc'd for $C_{11}H_{10}O_3N_2$: %C, 60.54; %H, 4.62; %N, 12.84. Found: %C, 60.48; %H, 4.70; %N, 12.33

B. To a stirred mixture of benzofuroxan (6.8 g., 0.05 mole) and acetyl acetone (5.0 g., 0.05 mole) in 40 ml. tetrahydrofuran is added n-propylamine (2.96 g., 0.05 mole). The reaction mixture is stirred overnight at room temperature and then evaporated under reduced pressure to a slurry. This residue is triturated with ether and filtered to recover 0.9 g. of yellow solid which, upon crystallization from chloroform-hexane, is reduced to 0.33 g. melting at 146°-149° C. (MIC against Vibrio comma is 3.12 mcg./ml.). Further purification is achieved by recrystallization from methanol.

C. Benzofuroxan (13.6 g., 0.10 mole), acetylacetone (12.0 g., 0.12 mole), ethanol (100 ml.) and sodium hydroxide (0.4 g., 0.01 mole) are charged into a three-neck, round-bottom flask equipped with thermometer, condenser, and magnetic stirrer. The reaction is conducted under an atmosphere of nitrogen. After about twenty minutes, the temperature rises to 30° C. followed by darkening of the mixture and formation of a yellow precipitate. The reaction mixture is stirred until the temperature returns to room temperature, then filtered to give 7.3 g. of crude product. When recrystallized from ethanol, it melts at 151°-153° C.

Additional product can be recovered from the filtrate.

EXAMPLE XIII

2-Methyl-3-Carboethoxyquinoxaline-di-N-Oxide

A. A solution of benzofuroxan (3.4 g.) and ethylacetoacetate (3.3 g.) in triethylamine (25 ml.) was allowed to stand at room temperature for 30 hours. The mother liquor was decanted and the resultant solid washed with water and recrystallized from acetone-water. The yield was 1.1 g. of yellow prisms melting at 132°-133° C. Another crop of product was obtained from the mother liquor after 18 hours. The total yield of 2-methyl-3-carboethoxyquinoxaline-di-N-oxide melting at 132°-133° C. was 1.4 g. or 22 percent.

Infrared: 1730, 1510, 1330, 1275, 1240, 1050, 1010, -1000, 770 $cm^{-1}$

Analysis: Calc'd for $C_{12}H_{12}N_2O_4$: %C, 58.06; %H, 4.87; %N, 11.29. Found: %C, 58.27; %H, 4.74; %N, 10.98.

B. To a solution of benzofuroxan (6.8 g., 0.05 mole) and ethylacetoacetate (6.51 g., 0.05 mole) in 40 ml. tetrahydrofuran is added n-propylamine (2.96 g., 0.05 mole). The reaction mixture is stirred for 36 hours and filtered to separate a trace of tan solid. The filtrate is evaporated at reduced pressure to a slurry and triturated with chloroform-hexane. After refrigeration storage, the slurry is filtered to recover 4.29 g. of product in the form of a tan solid which is purified by recrystallization from chloroform-hexane with activated carbon treatment.

C. Sodium metal pellets (2.3 g., 0.1 moles) are dissolved in 800 ml. of ethanol. To this resulting sodium ethoxide solution is added ethylacetoacetate (13.4 g., 0.1 moles) and then benzofuroxan (13.6 g., 0.1 moles) and the mixture is allowed to stand overnight. The material which precipitates is filtered, dried and recrystallized from ethanol to give good yields of product, M.P. 133°-134° C.

Analysis: Calc'd for $C_{12}H_{12}N_2O_4$: %C, 58.06; %H, 4.87; %N, 11.29. Found: %C, 58.15; %H, 4.84; %N, 11.16.

D. The procedure of method C above is repeated but using a stoichiometric equivalent amount of potassium hydroxide in place of sodium ethoxide with comparable results.

EXAMPLE XIV

Quinoxaline-di-N-Oxide

A mixture of benzofuroxan (2.5 g.), acetaldehyde (2.5 ml.) and triethylamine (20 ml.) is allowed to stand at room temperature for 24 hours. The solid material which precipitates is filtered and dried to give product, M.P. 223°-224° C. dec. (MIC against P. vulgaris is 12.5 mcg./ml.).

EXAMPLE XV

2-Methylquinoxaline-di-N-Oxide

A. A mixture of benzofuroxan (8.7 g.), propionaldehyde (13.6 g.) and diethylamine (60 ml.) is allowed to stand at room temperature for 24 hours. The solid material which precipitates is filtered and dried to give 8.0 of product. Recrystallization from a chloroform-acetone (1:1) mixture gives product having an M.P. 176°-178° C.

B. The procedure of Examples XIV and XV are repeated using gaseous $NH_3$ as the base. Comparable yields are obtained. The $NH_3$ is added over a 5-minute period once the reagents are combined with subsequent treatment as indicated.

EXAMPLE XVI

The procedure of Example XV is repeated wherein stoichiometric equivalent amounts of butyraldehyde and valeraldehyde are used in lieu of propionaldehyde and corresponding products, 2-ethylquinoxaline-di-N-oxide and 2-propylquinoxaline-di-N-oxide, respectively, are obtained in good yields.

EXAMPLE XVII

1-Hydroxybenzimidazole-3-Oxide

To a mixture containing nitromethane (7.4 g., 0.12 moles), benzofuroxan (13.6 g., 0.10 moles) and tetrahydrofuran (50 ml.) is slowly added dimethylpyrimidine (11.3 g.) dropwise. The heat of reaction causes the reaction temperature to rise sharply; therefore, an ice-bath is used to maintain a steady rate of reflux. Upon completion of addition, the resulting mixture is allowed to cool to room temperature whereupon the solid product which precipitates is filtered, washed with water, dried and recrystallized from a MeOH/$NaOCH_3$ mixture which is subsequently acidified. The crystalline product has an M.P. 213° C. dec.

Analysis: Calc'd. for $C_7H_6O_2N_2$: %C, 56.00; %H, 4.03; %N, 18.66. Found: %C, 56.13; %H, 4.06; %N, 18.77.

EXAMPLE XVIII

1-Hydroxy-2-Methylbenzimidazole-3-Oxide

To a mixture containing nitroethane (9.0 g., 0.12 moles), benzofuroxan (13.6 g., 0.10 moles) and tetrahydrofuran (50 ml.) is added dropwise diethylamine (8.7 g., 0.12 moles). The reaction temperature rises almost to reflux upon addition. Upon completion, the mixture is allowed to cool and to stand overnight.

The solid product which precipitates is filtered, washed with tetrahydrofuran and then dried. The filter cake is recrystallized from acetic acid to give 9.6 g. (45 percent) of product, M.P. 204°-205° C. dec.

Analysis: Calc'd. for $C_8H_8O_2N_2$: %C, 58.53; %H, 4.91; %N, 17.07. Found: %C, 58.38; %H, 4.95; %N, 16.70.

EXAMPLE XIX

1-Hydroxy-2-Ethylbenzimidazole-3-Oxide

To a mixture containing 1-nitropropane (10.7 g., 0.12 moles), benzofuroxan (13.6 g., 0.10 moles) and tetrahydrofuran (50 ml.) is added dropwise diethylamine (8.7 g., 0.12 moles). The reaction temperature rises almost to reflux on addition of amine. Upon completion, the mixture is allowed to cool and then sit overnight.

The solid product which precipitates is filtered, washed with tetrahydrofuran and then dried. The dried filter cake is recrystallized from acetic acid to give 10.95 g. (49 percent) of product, M.P. 194°-196° C. dec.

Analysis: Calc'd. for $C_9H_{10}O_2N_2$: %C, 60.66; %H, 5.66; %N, 15.72. Found: %C, 60.46; %H, 5.70; %N, 15.91.

EXAMPLE XX

1-Hydroxy-2-Propylbenzimidazole-3-Oxide

The procedure of Example XIX is repeated for the preparation of the subject compound wherein a stoichiometric equivalent amount of 1-nitrobutane is used in place of 1-nitropropane with comparative results.

EXAMPLE XXI

1-Hydroxy-2-Benzimidazole Propionamide-3-Oxide

To a mixture containing gamma nitro butyric acid amide (15.8 g., 0.12 moles), benzofuroxan (13.6 g., 0.10 moles) and dimethylformamide (75 ml.) is added dropwise diethylamine (8.7 g., 0.12 moles). The reaction temperature rises and is maintained at 55° C. with an ice-bath. Upon completion of addition, the mixture is allowed to cool and then sit overnight.

The solid product is filtered and a second crop is obtained by adding acetone to the filtrate. The two crops are combined, washed, dried and recrystallized from an acetone-acetic acid (1:1) mixture to give 12.5 g. (43 percent) of product, M.P. 215° C. dec.

Analysis: Calc'd. for $C_{10}H_{11}O_3N_3$: %C, 54.29; %H, 5.01; %N, 19.00. Found: %C, 54.56; %H, 5.09; %N, 19.00.

EXAMPLE XXII

1-Hydroxy-2-Carbethoxybenzimidazole-3-Oxide

A solution containing ethyl nitro acetate (4.22 g., 0.0317 moles), tetrahydrofuran (5 ml.) and triethylamine (5 ml.) is added to a solution of benzofuroxan (4.30 g., 0.0317 moles) in tetrahydrofuran (10 ml.) containing 10 ml. of triethylamine. Upon completion of addition, the reaction mixture is allowed to sit at room temperature for about 4 hours whereupon the yellow precipitated solid is filtered, washed and dried. Recrystallization from ether/acetone gives 1.1 g. (13 percent) of product, M.P. 154.5° C.-156.5° C. dec.

Analysis: Calc'd. for $C_{10}H_{10}O_4N_2$: %C, 54.05; %H, 4.54; %N, 12.61. Found: %C, 54.03; %H, 4.46; %N, 12.60.

EXAMPLE XXIII

2,2-Dimethyl-2H-Benzimidazole-1,3-Dioxide

To a mixture containing 2-nitropropane (10.7 g., 0.12 moles), benzofuroxan (13.6 g., 0.10 moles) and tetrahydrofuran (50 ml.) is added dropwise diethylamine (8.7 g., 0.12 mole). The reaction temperature rises during addition. Upon completion of addition, the reaction mixture is allowed to sit overnight at room temperature.

The solid product which precipitates is filtered, washed and dried to give 8.0 g. (33 percent) or product, M.P. 132°-134° C. dec. (MIC against Past. multocida is 3.12 mcg./ml.).

Analysis: Calc'd for $C_9H_{10}O_2N_2$: %C, 60.66; %H, 5.66; %N, 15.72. Found: %C, 60.67; %H, 5.64; %N, 15.98.

EXAMPLE XXIV

2,2-Methyl, Ethyl-2H-Benzimidazole-1,3-Dioxide

To a mixture containing 2-nitrobutane (6.2 g., 0.06 moles), benzofuroxan (6.8 g., 0.05 moles) and tetrahydrofuran (25 ml.) is added dropwise diethylamine (4.4 g., 0.06 moles). The reaction is exothermic. Upon completion of addition, the reaction mixture is allowed to sit for about 4 hours at room temperature. The resulting solution is evaporated almost to dryness, the solids filtered, washed, dried and recrystallized from an acetone/hexane mixture to give a good yield of product. (MIC against Past. multocida is 3.12 mcg./ml.).

EXAMPLE XXV

2,2-Pentamethylene-2H-Benzimidazole-1,3-Dioxide

To a mixture containing nitrocyclohexane (15.5 g., 0.12 moles) benzofuroxan (13.6 g., 0.10 moles) and tetrahydrofuran (50 ml.) is added dropwise 1,5-diazadibyclo [4,3,0]-5-nonene (0.10 moles). The reaction is exothermic and is cooled with an ice-bath to prevent temperature above 50° C.

Upon completion the reaction mixture is cooled and the filtrate allowed to sit overnight. After this time the filtrate is filtered again and then evaporated almost to dryness. The oil crystallizes on standing and is filtered, washed and dried to give a good yield of product, M.P. 112°-115° C. (MIC against Past. multocida is 6.25 mcg./ml.).

Analysis: Calc'd for $C_{12}H_{14}O_2N_2$: %C, 66.03; %H, 6.47; %N, 12.84. Found: %C, 65.95; %H, 6.59; %N, 12.95.

The procedures of Examples XVII-XXV are repeated wherein ammonia gas is used in place of the organic amines indicated with comparable results. The ammonia is added over a 5-minute period to the combined reagents (and solvent) through a dispersion tube. On completion, the reaction is carried out as indicated.

EXAMPLE XXVI

2-Cyano-3-Aminoquinoxaline-di-N-Oxide

A mixture of malononitrile (20.0 g., 0.3 moles), benzofuroxan (34.0 g., 0.25 moles), triethylamine (10 ml.) and tetrahydrofuran (200 ml.) is stirred at room temperature. After approximately 30 minutes, the reaction mixture becomes violently exothermic and must be controlled with an ice-bath. After a while the ice-bath is removed and the mixture allowed to stand for about 24 hours. The material which precipitates is filtered and dried. Recrystallization from methanol gives product, M.P. 239° C. dec. (MIC against Ps. aeruginosa is 6.25 mcg./ml.).

Analysis: Calc'd for $C_9H_6O_2N_4$: %C, 53.46; %H, 2.99; %N, 27.72. Found: %C, 53.52; %H, 3.47; %N, 27.42.

EXAMPLE XXVII

2-Carbomethoxymethyl-3-Carbomethoxyquinoxaline-di-N-Oxide

A mixture of benzofuroxan (13.6 g.) dimethylacetonedicarboxylate (50 ml.) and morpholine (5 ml.) is stirred for about 2 to 3 hours (exothermic) and is then thinned out by adding 200 ml.) of benzene. The material which precipitates is filtered, dried and recrystallized from acetonitrile, M.P. 152.3°-153.5° C. (MIC against *Past. multocida* is 1.56 mcg./ml.).

Analysis: Calc'd for $C_{13}H_{12}O_6N_2$: %C, 53.42; %H, 4.14; %N, 9.59. Found: %C, 53.37; %H, 4.27; %N, 9.74.

EXAMPLE XXVIII

2-[2'-(1"-Pyrrolidyl)Ethylene]Quinoxaline-di-N-Oxide

A solution of benzofuroxan (13.6 g., 0.1 mole) and 2-keto-4-dimethoxybutane (13.2 g., 0.1 mole) in tetrahydrofuran (150 ml.) is treated with pyrrolidine (14.2 g., 0.2 mole) and the reaction mixture is allowed to stand for three days at room temperature. It is then poured over crushed ice and the product extracted with chloroform. The extract is stripped of chloroform and the resulting crude product purified by recrystallization from chloroform-hexane.

EXAMPLE XXIX

2-N-Phenylcarbamyl-3-Methylquinoxaline-di-N-Oxide

A mixture of benzofuroxan (13.6 g.), acetoacetanilide (17.7 g.), diethylamine (10 ml.) and tetrahydrofuran (100 ml.) is allowed to stand for about 2 hours. The material which precipitates is filtered, dried and recrystallized from a chloroform-methanol (1:1) mixture, M.P. 226°-227° C. dec.

Analysis: Calc'd. for $C_{16}H_{13}O_3N_3$: %C, 65.08; %H, 4.44; %N, 14.23. Found: %C, 65.01; %H, 4.58; %N, 14.14.

EXAMPLE XXX

2-N-(p-Methylphenyl)Carbamyl-3-Methylquinoxaline-di-N-Oxide

The procedure of Example XXIX is repeated except a stoichiometric equivalent amount of p-acetoacetotoluidide is used in place of acetoacetanilide. Good yields of product are obtained, M.P. 196°-198° C.

Analysis: Calc'd. for $C_{17}H_{15}O_3N_3$: %C, 66.01; %H, 4.89; %N, 13.59. Found: %C, 66.24; %H, 4.89; %N, 13.40.

EXAMPLE XXXI

2-N-(o-Methoxyphenyl)Carbamyl-3-Methylquinoxaline-di-N-Oxide

The procedure of Example XXIX is repeated except a stoichiometric equivalent amount of o-acetoacetanisidide is used instead of acetoacetanilide. Good yields of product are obtained, M.P. 197°-199° C.

Analysis: Calc'd. for $C_{17}H_{15}O_4N_3$: %C, 62.76; %H, 4.65; %N, 12.92. Found: %C, 62.93; %H, 4.66; %N, 12.68.

EXAMPLE XXXII

2-N-Cyclohexylcarbamyl-3-Methylquinoxaline-di-N-Oxide

The procedure of Example XXIX is repeated except a stoichiometric equivalent amount of acetoacetocyclohexylamine is used in place of acetoacetanilide. Substantial yields of product are obtained, M.P. 204.5°-206° C.

Analysis: Calc'd. for $C_{16}H_{18}O_3N_3$: %C, 63.98; %H, 6.04; %N, 13.99. Found: %C, 63.68; %H, 6.49; %N, 13.93.

EXAMPLE XXXIII

2-N-(6-Ethoxybenzothiazole)Carbamyl-3-Methylquinoxaline-di-N-Oxide

The procedure of Example XXIX is repeated except a stoichiometric equivalent amount of 2-acetoacetamido-6-ethoxybenzothiazole is used in place of acetoacetanilide. Substantial yields of product are obtained, M.P. 235°-237° C. dec.

Analysis: Calc'd. for $C_{19}H_{16}O_4N_4S$: %C, 57.60; %H, 4.07; %N, 14.14; %S, 8.08. Found: %C, 57.67; %H, 4.19; %N, 14.20; %S, 8.07.

EXAMPLE XXXIV

2-N-(t-butyl)Carbamyl-3-Methylquinoxaline-di-N-Oxide

The procedure of Example XXIX is repeated except a stoichiometric equivalent amount of N-t-butylacetoacetamide is used in lieu of acetoacetanilide. Substantial yields of product are obtained, M.P. 224.5°-225.5° C. dec. (MIC against *Past. multocida* is 12.5 mcg./ml.).

Analysis: Calc'd. for $C_{14}H_{17}O_3N_3$: %C, 61.08; %H, 6.22; %N, 15.26. Found: %C, 60.84; %H, 6.30; %N, 15.10.

EXAMPLE XXXV

2-N-Piperidinocarbonyl-3-Methylquinoxaline-di-N-Oxide

The procedure of Example XXIX is repeated wherein stoichiometric equivalent amounts of acetoacetopiperidide and piperidine are used in place of acetoacetanilide and diethylamine, respectively, and substantial yields of product are obtained, M.P. 174°-176° C. (MIC against *Past. multocida* is 100 mcg./ml.).

Analysis: Calc'd. for $C_{15}H_{17}O_3N_3$: %C, 62.70; %H, 5.96; %N, 14.63. Found: %C, 62.92; %H, 6.13; %N, 14.41.

EXAMPLE XXXVI

2-Carbomethoxy-3-Hydroxyquinoxaline-di-N-Oxide

A mixture of dimethylmalonate (14.5 g., 0.11 mole), benzofuroxan (13.6 g., 0.1 mole), sodium methoxide (5.4 g., 0.1 mole) and methanol (300 ml.) is allowed to stand overnight. The precipitated sodium salt of 2-carbomethoxy-3-hydroxyquinoxaline is separated by filtration and the product is isolated by acidification of the filtrate with 2 N hydrochloric acid followed by extraction with chloroform. Evaporation of the solvent from the extract yields the crude product, which is purified by crystallization from chloroform-hexane.

EXAMPLE XXXVII

2-Carboethoxy-3-Hydroxyquinoxaline-di-N-Oxide

This product is prepared in the same manner as that of the preceding example, substituting sodium ethoxide in ethanol for the sodium methoxide in methanol and diethylmalonate for dimethylmalonate.

EXAMPLE XXXVIII

2-Formyl-Quinoxaline-di-N-Oxide

Method A 13.6 g. benzofuroxan (0.1 mole) 11.8 g. pyruvaldehyde dimethylacetal (0.1 mole) 100 ml. acetonitrile.

To the above mixture is added 0.05 mole pyrrolidine and the reaction mixture is allowed to stand overnight at room temperature. The solvent is stripped in vacuo and the residue is dissolved in 25 ml. conc. hydrochloric acid. The solution is diluted with water and extracted with chloroform. The extract is stripped of chloroform to obtain crude 2-formylquinoxaline-di-N-oxide, which is purified by crystallization from chloroform-hexane.

Method B

The reaction procedure of Method A is repeated, substituting 21.8 g. $\gamma,\gamma$-diethoxy ethylacetoacetate (0.1 mole) for the pyruvaldehyde dimethylacetal. After standing overnight at room temperature, the reaction mixture is stripped in vacuo and the concentrate is heated on the steambath for 15 to 30 minutes, cooled, and diluted with water. The product is recovered and purified as before by chloroform extraction and chloroform-hexane crystallization.

Method C

The reaction procedure of Method B is repeated, substituting 0.1 mole sodium ethoxide for the pyrrolidine, and substituting ethanol for the acetonitrile reaction medium. The reaction mixture is heated at reflux temperature for 3 hours and concentrated in vacuo. The residue is dissolved in 50 ml. concentrated hydrochloric acid, heated 15 to 30 minutes on the steam-bath, cooled and diluted with water. Chloroform extraction and chloroform-hexane crystallization as before yields the product.

EXAMPLE XXXIX 2,3,6-(or 7-)Trimethylquinoxaline-di-N-Oxide

A mixture of 5-methylbenzofuroxan (1.5 g., 0.01 moles), methyl ethyl ketone (7 ml.) and pyrrolidine (2 drops) is stirred at room temperature overnight. The product which precipitates is filtered and recrystallized from an acetone-methanol (1:1) mixture, M.P. 193°-194° C.

Analysis Calc'd. for $C_{11}H_{12}N_2O_2$: %C, 64.69; %H, 5.93; %N, 13.72. Found: %C, 64.77; %H, 5.78; %N, 13.69.

EXAMPLE XL 2,3-Dimethyl, 6-(or 7-)Methoxyquinoxaline-di-N-Oxide

The procedure of Example XXXIX is repeated wherein a stoichiometric equivalent amount of 5-methoxybenzofuroxan is used in lieu of 5-methylbenzofuroxan with comparable results. The product is recrystallized from an acetone-methanol (1:1) mixture, M.P. 209°-210° C. dec.

Analysis: Calc'd. for $C_{11}H_{12}N_2O_3$: %C, 59.99; %H, 5.49; %N, 12.72. Found: %C, 60.38; %H, 5.51; %N, 12.63.

EXAMPLE XLI

2-Acetyl-3-Methyl-6-(or 7-)Methoxyquinoxaline-di-N-Oxide

5-Methoxybenzofuroxan (8.3 g., 0.05 mole) and acetylacetone (5 g., 0.05 mole) are added to 100 ml. of a 0.5 molar solution of sodium methoxide in methanol and the mixture is heated at reflux temperature for 3 hours. After cooling in an ice-salt bath, the reaction mixture is filtered to recover the product.

EXAMPLE XLII

2-Acetyl-3,5-Dimethylquinoxaline-di-N-Oxide

The procedure of Example XLI is repeated with substitution of 7.5 g. (0.05 mole) of 4-methylbenzofuroxan for the 5-methoxybenzofuroxan, and the product is recovered as before.

EXAMPLE XLIII

2-Acetyl-3,6,7-Trimethylquinoxaline-di-N-Oxide

The procedure of Example XLI is repeated, this time substituting 8.2 g. (0.05 mole) of 5,6-dimethylbenzofuroxan for the benzofuroxan of that example and the product is recovered as before. (MIC against *Past. multocida* is 50 mcg./ml.)

EXAMPLE XLIV

6-Acetyl-1,2,3,4-Tetrahydrophenazine-di-N-Oxide

A mixture containing 5-acetylbenzofuroxan (8.2 g., 0.05 mole) cyclohexanone (5.9 g., 0.06 mole), morpholine (4.3 g.) in 300 ml. benzene is refluxed for two hours, allowed to cool and then evaporated almost to dryness. The solid product is triturated with 1:1 acetone:Ether and the purified solid product recovered by filtration.

EXAMPLE XLV

6-Chloro-1,2,3,4-Tetrahydrophenazine-di-N-Oxide

This product is prepared by the procedure of Example XLIV with substitution of 8.6 g. (0.05 mole) of 5-chlorobenzofuroxan for the 5-acetylbenzofuroxan of that example and the product is recovered as before.

EXAMPLE XLVI

2-Carbethoxy-3-Formyldiethylacetalquinoxaline-di-N-Oxide

γ,γ-diethoxyethylacetoacetate (10.8 g., 0.05 mole) and benzofuroxan (6.8 g., 0.05 mole) are added to 50 ml. of a 0.005 molar solution of sodium ethoxide in ethanol, with stirring under nitrogen. The reaction mixture is stirred for three hours at room temperature and then heated at reflux temperature for three additional hours. After cooling to room temperature, the reaction mixture is stirred overnight and concentrated on the steam-bath to a viscous oil. Upon cooling, the oil solidifies and the resulting solid is slurried with ethanol, broken up, and the purified solid recovered by filtration. 9.8 Grams of yellow solid are obtained and purified by crystallization from acetone-hexane, with activated carbon treatment, to yield 8.3 grams, melting at 120°-123° C. Recrystallization from acetone-hexane gives 7.19 grams, melting at 120.5°-123.5° C. Analysis, calculated for $C_{16}H_{20}O_6N_2$: carbon, 57.14; hydrogen, 5.95; and nitrogen 8.33 percent; found: carbon, 57.38; hydrogen, 6.06; and nitrogen, 8.35 percent.

EXAMPLE XLVII

Method A—2-Methyl-Quinoxaline-di-N-Oxide

A mixture containing propionaldehyde (2.90 g., 0.05 mole), n-propylamine (2.96 g., 0.05 mole), and benzofuroxan (6.8 g., 0.05 mole) in 40 ml. tetrahydrofuran is stirred 3 hours at room temperature and filtered to recover 3.86 grams of solid product, melting at 174°-177° C. after washing with diethyl ether.

Method B

The mixture employed in Method A is again prepared, this time substituting for the propylamine 6.21 grams of 1,5-diaza-bicyclo[4,3,0]-5-nonene (0.05 mole). This mixture is stirred overnight at room temperature and the resulting yellow solid is separated by filtration, washed with ether and dried to yield 1.12 gram of product, melting at 135°-143° C. It is further purified by recrystallization from chloroform-hexane.

Method C

A mixture of benzofuroxan and propionaldehyde in tetrahydrofuran in the same proportions as before is treated with 3.24 ml. ammonium hydroxide (29.5 percent $NH_3$) and stirred at room temperature for 4½ days. The resulting slurry is filtered to yield 1.55 gram of product melting at 163°-165° C. It is purified by recrystallization from chloroform-hexane.

Method D—2-Methyl-Quinoxaline-Dioxide

To a solution of benzofuroxan (6.8 g., 0.05 mole) in 40 ml. acetone is added 3.24 ml. ammonium hydroxide (29.5 percent $NH_3$). The reaction mixture is stirred for 4½ days and filtered to recover 1.16 gram of product melting at 161°-164.5° C.

Method E

A solution of benzofuroxan (13.61 g., 0.1 mole) in 80 ml. acetone is treated with ammonia gas, introduced through a dispersion tube over a 10-minute period. The reaction mixture is left standing under a drying tube for 3 days at room temperature and 6.47 grams of product melting at 162°-165° C. are recovered by filtration.

Method F

To a solution of benzofuroxan (3.4 g., 0.025 mole) in 50 ml. acetone is added 1.5 g. n-propylamine. The reaction mixture is stirred overnight at room temperature and the resulting slurry is filtered and the cake washed with ether. This provides 0.52 grams of pale yellow solid product melting at 176°-178° C. A second fraction (0.83 gram melting at 160°-163.5° C.) is obtained by evaporation of the filtrate under vacuum to dryness, trituration of the resulting solid with ether and filtration.

The above products of Methods D through F are purified by recrystallization from chloroform-hexane.

EXAMPLE XLVIII

2-Oximinomethylquinoxaline-di-N-Oxide

Method A

A solution of benzofuroxan (13.6 g., 0.1 mole) and isonitrosoacetone (9.0 g., 0.1 mole) in 100 ml. tetrahydrofuran is treated with ammonia gas introduced through a dispersion tube over a 10-minute period. After standing for 20 hours at room temperature in a pressure bottle, the reaction mixture is filtered to obtain 8.0 grams of product in the form of brown crystals melting at 239°-240° C. (MIC against *Past. multocida* is 12.5 mcg./ml.).

Method B

The procedure of Method A is repeated, this time with the substitution of 0.1 mole of morpholine for the ammonia gas, with substantially the same result.

Method C

The procedure of Method A is repeated a second time, now substituting 0.1 mole pyrrolidine in place of the ammonia gas, with recovery of the same product as before.

EXAMPLE XLIX

2-Formyl-Dimethylacetalquinoxaline-di-N-Oxide

A series of preparations is conducted, in each case dissolving benzofuroxan (13.6 g., 0.1 mole) and pyruvaldehyde dimethylacetal (11.8 g., 0.1 mole) in the indicated volume of solvent, with addition of base as indicated in the table below. Where ammonia gas is the chosen base, it is introduced into the solution through a dispersion tube over a 10-minute period. Where pyrrolidine is the base selected, 2 ml. are added to the solution. In each run, the reaction mixture is permitted to stand overnight at room temperature and the product then recovered by evaporation under vacuum to dryness followed by ether trituration and separation of the resulting solid product by filtration. The individual runs are summarized in the table.

| | Solvent | Base | Yield % of Theory | Product Melting Point |
|---|---|---|---|---|
| 1. | 50 ml. chloroform | pyrrolidine | 61% | 128-130° C. |
| 2. | 100 ml. diethyl ether | pyrrolidine | 71% | 140-141° C. |
| 3. | 100 ml. methanol | pyrrolidine | 39% | 128-134° C. |
| 4. | 50 ml. tetrahydrofuran | pyrrolidine | 51% | 127-131° C. |
| 5. | 50 ml. acetonitrile | pyrrolidine | 68% | 120-128° C. |
| 6. | 50 ml. methanol | $NH_3$ | 27.5% | 138-140° C. |

The product of run 2, above, is recrystallized from benzene to yield a purified sample melting at 142°-143° C. Analysis, calculated for $C_{11}H_{12}N_2O_4$: carbon, 55.93; hydrogen, 5.12; nitrogen, 11.86; and oxygen, 27.09 percent; found: carbon, 56.22; hydrogen, 5.15; nitrogen, 11.78; and oxygen, 26.85 percent. The remaining products are also purified by recrystallization from benzene.

EXAMPLE L

2-Methyl-3-(2'-pyrrolidyl)-n-Propylquinoxaline-di-N-Oxide

To a solution of benzofuroxan (6.8 g., 0.05 mole) and allylacetone (4.9 g., 0.05 mole) in 100 ml. tetrahydrofuran is added 7.1 g. pyrrolidine with cooling in an ice-bath. The reaction mixture is stirred overnight at room temperature and concentrated to remove the tetrahydrofuran. The resulting concentrate is fractionated by chromatography in benzene on a 30×4 cm. cylindrical column of Florisil (an activated magnesium silicate available from the Floridin Co., of Tallahassee, Fla.). The chromatogram is developed with benzene, as 150-200 ml. effluent fractions are collected. Each fraction is evaporated and the product residues are selected on the basis of ultraviolet absorption in methanol solution (those having max=378 mμ). The product fractions are combined and purified by recrystallization from ether to yield 297 mg. of product melting at 99°-101° C.

Analysis, calculated for $C_{16}H_{21}O_2N_3$: carbon, 66.87; hydrogen, 7.37; and nitrogen, 14.62 percent; found: carbon, 66.83; hydrogen, 7.29; and nitrogen, 14.48 percent.

EXAMPLE LI

2-(2'-diethylaminoethylene)Quinoxaline-di-N-Oxide

A solution of benzofuroxan (1.36 g., 0.01 mole), crotonaldehyde (2.0 g.) and diethylamine (3.0 g.) in 20 ml. tetrahydrofuran is stirred at room temperature overnight. The resulting slurry is filtered to recover 650 mg. of orange-red solid, which is purified by recrystallization from chloroform-hexane. The resulting 0.5 g. of product melts at 188°-190.5° C. with decomposition.

Analysis, calculated for $C_{14}H_{17}O_2N_3$: carbon, 64.86; hydrogen, 6.56; and nitrogen, 16.22 percent; found: carbon, 64.67; hydrogen, 6.99; and nitrogen, 16.11 percent.

EXAMPLE LII

2-Methyl-3-Cyclopentylquinoxaline-di-N-Oxide

A mixture of cyclopentyl acetone (12.6 g., 0.1 mole), isobenzofuroxan (13.6 g., 0.1 mole) and pyrrolidine (1.57 g., 0.025 mole) in 100 ml. tetrahydrofuran is stirred at room temperature overnight. The reaction mixture is then combined with an equal volume of 2 N hydrochloric acid and extracted with chloroform. The chloroform extract is dried over anhydrous sodium sulfate, treated with activated carbon and filtered. The filtrate is evaporated to dryness and the resulting solid residue is triturated with ether and the slurry filtered. The resulting 4 grams of yellow-green solid is dissolved in chloroform and treated with activated carbon. The slurry is filtered and the filtrate crystallized by addition of chloroform-hexane. 2.73 Grams of dark yellow crystalline solid melting at 156°-158° C. is separated by filtration.

Analysis, calculated for $C_{14}H_{16}O_2N_2$: carbon, 68.83; hydrogen, 6.60; and nitrogen, 11.47 percent; found: carbon, 68.91; hydrogen, 6.50; and nitrogen, 11.26 percent.

EXAMPLE LIII

2-Carbethoxy-1,2,3,4-Tetrahydrophenazine-di-N-Oxide

To a solution of benzofuroxan (13.6 g., 0.1 mole) and 4-carbethoxy cyclohexanone (15 g.) in 100 ml. acetonitrile is added 2 ml. pyrrolidine. After about 15 minutes, an exothermic reaction ensues. The reaction mixture is stored overnight at room temperature and evaporated under vacuum to a semi-solid, which is triturated with ether to yield 8.55 grams of solid product melting at 140°-150° C. Purification by recrystallization gives a product melting at 156°-160° C.

EXAMPLE LIV

2-Acetyl-3-Methyl-6-Trifluoromethylquinoxaline-di-n-Oxide and 2-Acetyl-3-Methyl-7-Trifluoromethylquinoxaline-di-N-Oxide

A.

A solution of 20.4 grams (0.1 mole) of 5-trifluoromethylbenzofuroxan, 12.0 grams (0.12 moles) of acetylacetone, 100 ml. of anhydrous ethanol and 1.0 ml. of 10 N sodium hydroxide is stirred and a spotaneous temperature rise to 46° C. is observed initially. After a few hours the temperature drops to 25° C. After stirring overnight at room temperature, the reaction mixture is evaporated under reduced pressure and the oily residue is triturated under ether. After cooling in an ice-bath, crystals are slowly formed; yield 5.3 grams, M.P. 137°-140° C. This product is recrystallized from 2-propanol to afford 1.8 grams of material, M.P. 153°-154° C. A further recrystallization from chloroform-hexane afforded 0.7 grams of 2-acetyl-3-methyl-6-trifluoromethylquinoxaline-di-N-oxide, M.P. 167°-168° C.

Analysis: Calc'd. for $C_{12}H_9F_3N_2O_3$: %C, 50.35; %H, 3.17; %N, 9.79. Found: %C, 50.52; %H, 3.16; %N, 9.66.

From the initial ether filtrate a second crude product is obtained, yield: 6.5 grams, M.P. 117°-121° C. This is recrystallized three times from 2-propanol to furnish pure 2-acetyl-3-methyl-7-trifluoromethylquinoxaline-di-N-oxide, yield, 1.5 grams, M.P. 152°-153° C. Mixed melting points of the isomeric trifluoromethyl compounds at 141°-142° C.

Analysis: Calc'd. for $C_{12}H_9F_3N_2O_3$: %C, 50.35, %H, 3.17; %N, 9.79. Found: %C, 50.56; %H, 3.30; %N, 9.80.

B. Preparation of 5-Trifluoromethylbenzofuroxan Starting Material

A solution of 103 grams (0.5 mole) of 4-amino-3-nitrobenzotrifluoride, 750 ml. of acetic acid and 385 ml. of concentrated sulfuric acid is cooled in an ice-bath with sufficient stirring. Sodium nitrite (38 grams, 0.55 moles) is added portionwise at such a rate that the reaction temperature does not exceed 5° C. After addition is complete, 38 grams of urea is added, and with vigoroug stirring 32.5 grams of sodium azide is then added. Stirring is continued for 20 minutes, then the reaction mixture is poured into 4 liters of ice and water. The crude product, 4-azido-3-nitrobenzotrifluoride is extracted from the aqueous mixture with chloroform. The extract is dried over anhydrous sodium sulfate, filtered and evaporated under reduced pressure to furnish an oily-residue which is taken up in 800 ml. of toluene. The toluene solution is heated under reflux for 18 hours behind a shatter-proof shield. After cooling to room temperature, the solvent is evaporated and the residue is distilled under reduced pressure. The fraction boiling at 105°-108° C. (16 ml.) is considered to be sufficiently pure 5-trifluoromethylbenzofuroxan; yield, 62.3 (60 percent).

EXAMPLE LV

The procedure of Example XXIX is repeated but using the appropriate N-substituted acetoacetamide in place of acetoacetanilide to give the following products:

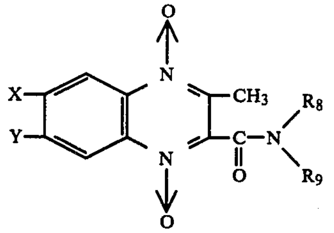

| X | Y | $R_8$ | $R_9$ | M.P. (°C.) |
|---|---|---|---|---|
| H | H | $CH_3$ | H | 223 |
| H | H | $C_2H_5$ | H | 213-4 |
| H | H | $n-C_3H_7$ | H | 175 |
| H | H | $CH_3$ | $CH_3$ | 193-4 |
| H | H | $C_2H_5$ | $C_2H_5$ | 162-4 |
| H | H | $i-C_3H_7$ | H | 217-8 |
| H | H | $n-C_4H_9$ | H | 148 |
| H | H | $C_7H_7$ | H | 218-9 |
| Cl | H | $CH_3$ | H | 220-1 |
| $OCH_3$ | H | $CH_3$ | H | 236-7 |
| Br | H | $C_2H_5$ | H | 207 |
| F | H | $C_2H_5$ | H | 222-3 |
| Cl | H | $CH_3$ | $CH_3$ | 194-5 |
| Cl | H | $C_2H_5$ | $C_2H_5$ | 169-70 |
| $OCH_3$ | H | H | H | 262 |
| $CF_3$ | H | H | H | 230 |
| F | H | H | H | 243-4 |
| F | H | $CH_3$ | H | 232-3 |
| Br | H | H | H | 237 |
| Cl | H | H | H | 237 |
| $CH_3$ | H | H | H | 246 |
| $CH_3$ | $CH_3$ | H | H | 263-4 |
| Cl | Cl | H | H | 251 |
| $OCH_3$ | H | H | $C_2H_5$ | 233 |
| Br | H | $CH_3$ | H | 223 |
| Cl | Cl | H | $CH_3$ | 225 |
| Cl | H | H | $C_2H_5$ | 216-8 |
| Cl | Cl | H | $C_2H_5$ | 220 |
| Cl | H | H | $n-C_3H_7$ | 208 |
| Cl | H | H | $i-C_3H_7$ | 216-7 |
| H | H | H | $i-C_4H_9$ | 156-7 |
| H | H | H | $sec-C_4H_9$ | 199-200 |
| H | H | H | allyl | 154 |
| Cl | H | H | allyl | 165 |
| H | H | $-CH_2CH_2CH_2CH_2-$ | | 188-9 |
| Cl | H | $-CH_2CH_2CH_2CH_2-$ | | 214-5 |
| H | H | $-CH_2CH_2CH_2CH_2CH_2-$ | | 174-6 |
| Cl | H | $-CH_2CH_2CH_2CH_2CH_2-$ | | 218 |
| H | $SO_2NH_2$ | H | H | 230-2 |
| H | $SO_2NH_2$ | $CH_3$ | H | 216-7 |
| H | $SO_2NH_2$ | $CH_3$ | $CH_3$ | 220-2 |
| H | $SO_2NH(CH_3)$ | H | H | 215-7 |
| H | $SO_2NH(CH_3)$ | $CH_3$ | H | 209-10 |
| H | $SO_2NH(CH_3)$ | $CH_3$ | $CH_3$ | 227-9 |
| H | $SO_2N(CH_3)_2$ | H | H | 232-3 |
| H | $SO_2N(CH_3)_2$ | $CH_3$ | $CH_3$ | 222-3 |
| H | $SO_2N(CH_3)_2$ | H | $n-C_4H_9$ | 167-9 |
| H | $SO_2N(CH_3)_2$ | H | $n-C_3H_7$ | 195-7 |
| H | $SO_2N(CH_3)_2$ | H | $C_2H_5$ | 201-3 |

EXAMPLE LVI

The quinoxaline-di-N-oxides listed below are prepared by the procedure of Example XIV from the appropriate aldehyde ($R_1CH_2CHO$) or ketone ($R_1CH_2COR_2$) and benzofuroxan or a substituted benzofuroxan.

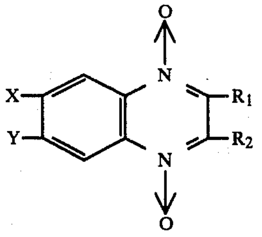

| $R_1$ | $R_2$ | X | Y |
|---|---|---|---|
| $CH_3$ | H | $CONH_2$ | H |
| $C_2H_5$ | H | $OCH_3$ | Cl |
| $C_7H_{15}$ | H | H | H |
| $C_7H_{15}$ | H | Cl | H |
| n-$C_4H_9$ | H | Br | H |
| n-$C_4H_9$ | H | $CH_3$ | $CH_3$ |
| $CH_3$ | H | $OC_2H_5$ | H |
| $CH_2OH$ | H | Cl | H |
| $CH_2OH$ | H | $OCH_3$ | H |
| $CH_2OH$ | H | $CF_3$ | H |
| $CH_2CH_2OH$ | H | $OCH_3$ | H |
| $CH_2CH_2OH$ | H | Cl | H |
| $CH_2OCH_3$ | H | H | H |
| $CH_2OCH_3$ | H | $CONH_2$ | H |
| $(CH_2)_3OCH_3$ | H | Cl | H |
| $(CH_2)_3OCH_3$ | H | Cl | Cl |
| $CH_2OCOCH_3$ | H | F | H |
| $CH(OC_2H_5)CH_3$ | H | H | H |
| $CH(OC_2H_5)CH_3$ | H | Cl | H |
| $CH(OCH_3)_2$ | H | F | H |
| $CH_2OCH_3$ | H | $CF_3$ | H |
| $CH_3$ | H | $OCH_3$ | Cl |
| $CH_2NHCH_3$ | H | H | H |
| $CH_2NHCH_3$ | H | $OCH_3$ | H |
| $CH_2NH_2$ | H | H | H |
| $CH_2NH_2$ | H | F | H |
| $CH_2CN$ | H | $CH_3$ | $CH_3$ |
| $CH_2CN$ | H | F | H |
| $CH_2CN$ | H | $CF_3$ | H |
| $CH_2COOCH_3$ | H | H | H |
| $CH_2COOCH_3$ | H | Cl | Cl |
| $CH_2COOC_2H_5$ | H | $OCH_3$ | H |
| $CH_2COOC_2H_5$ | H | F | H |
| $CH_2OCH_3$ | H | $OC_2H_5$ | Cl |
| $CH_2OCH_3$ | H | Cl | $CH_3$ |
| $CH_2OCH_3$ | H | $OC_2H_5$ | H |
| $CH_2CH_2OCH_3$ | H | F | H |
| $CH_2CH_2OCH_3$ | H | Cl | H |
| $CH_2CH_2OCH_3$ | H | $CONH_2$ | H |
| $CH_2CH_2OCH_3$ | H | H | H |
| $CH_2OH$ | H | $OC_2H_5$ | Cl |
| $CH_2OH$ | H | $SO_2NH_2$ | H |
| $CH_2OH$ | H | $SO_2NHCH_3$ | H |
| $CH_2OH$ | H | $SO_2N(CH_3)_2$ | H |
| $CH_2CH_2OH$ | H | $SO_2N(CH_3)_2$ | H |
| $CH_2CH_2OCOCH_3$ | H | $SO_2N(CH_3)_2$ | H |
| $CH_2CH_2OCOCH_3$ | H | $SO_2NH_2$ | H |
| $CH_2CH_2OCOCH_3$ | H | $CF_3$ | H |
| $CH(OC_2H_5)CH_3$ | H | $CF_3$ | H |
| $CH(OC_2H_5)CH_3$ | H | $SO_2N(CH_3)_2$ | H |
| $CH_2NHCH_3$ | H | $SO_2N(CH_3)_2$ | H |
| $CH_2CN$ | H | $SO_2NH_2$ | H |
| $CH_2OCH_3$ | H | $SO_2NHCH_3$ | H |
| $CH_2OCH_3$ | H | $SO_2NH_2$ | H |
| $CH_2CH_2OCH_3$ | H | $SO_2N(CH_3)_2$ | H |
| $CH_2NHCH_3$ | H | $SO_2NH_2$ | H |
| $CH_2CH_2OCH_3$ | H | $CF_3$ | H |
| $CH(OC_2H_5)_2$ | $CH_3$ | H | H |
| $CH(OC_2H_5)_2$ | $CH_3$ | Cl | H |
| $CH(OC_2H_5)_2$ | $CH_3$ | $OCH_3$ | H |
| $CH(OC_2H_5)_2$ | $CH(CH_3)_2$ | H | H |
| $CH(OC_2H_5)_2$ | $CH(CH_3)_2$ | F | H |
| $CH(OC_2H_5)_2$ | $CH(CH_3)_2$ | $CH_3$ | H |
| $CH(OC_2H_5)_2$ | $CH_2C_6H_5$ | H | H |
| $CH(OC_2H_5)_2$ | $CH_2C_6H_5$ | $OCH_3$ | H |
| $CH(OC_2H_5)_2$ | $CH_2C_6H_5$ | Cl | H |
| $CH(OC_2H_5)_2$ | $CH_3$ | $SO_2N(CH_3)_2$ | H |
| $CH_3$ | $C_7H_{15}$ | H | H |
| $CH_3$ | $C_7H_{15}$ | Cl | H |

-continued

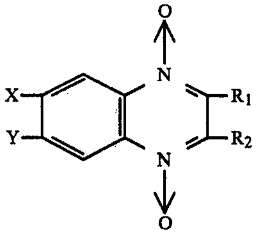

| $R_1$ | $R_2$ | X | Y |
|---|---|---|---|
| $CH_3$ | $C_7H_{15}$ | $CF_3$ | H |
| $CH_2OCH_3$ | H | $CH_3$ | H |
| $CH_2OCH_3$ | H | F | H |
| $CH_2OCH_3$ | H | $SO_2NH_2$ | H |
| $CH_2OCH_3$ | H | $CF_3$ | H |
| $CH_2OCH_3$ | H | $OCH_3$ | H |
| $CH_2N(CH_3)_2$ | H | H | H |
| $CH_2N(CH_3)_2$ | H | $OC_2H_5$ | H |
| $CH_2N(CH_3)_2$ | H | Cl | H |
| $CH_2N(CH_3)_2$ | H | $SO_2N(CH_3)_2$ | H |
| $CH_2COOH$ | H | H | H |
| $CH_2COOCH_3$ | H | H | H |
| $CH_2COOCH_3$ | H | Cl | H |
| $CH_2COOCH_3$ | H | $OCH_3$ | H |
| $CH_2COOCH_3$ | H | $CF_3$ | H |
| $CH_2CN$ | H | H | H |
| $CH_2CN$ | H | $OCH_3$ | H |
| $CH_2Cn$ | H | Cl | $OCH_3$ |
| $CH_2OC_6H_5$ | H | H | H |
| $CH_2OC_6H_5$ | H | Cl | H |
| $CH(OC_2H_5)CH_3$ | H | H | H |
| $CH(OC_2H_5)CH_3$ | H | Cl | H |
| $CH(OC_2H_5)CH_3$ | H | $OCH_3$ | H |
| $CH(OC_2H_5)CH_3$ | H | $SO_2NH_2$ | H |
| o-$ClC_6H_4$ | H | H | H |
| m-$CF_3C_6H_4$ | H | H | H |
| m-$CF_3C_6H_4$ | H | Cl | H |
| $CH_2OH$ | H | H | H |
| $CH_2N(CH_3)_2$ | $CH_3$ | H | H |
| $CH_2N(CH_3)_2$ | $CH_3$ | $OCH_3$ | H |
| $CH_2N(CH_3)_2$ | $CH_3$ | F | H |
| $CH_2N(CH_3)_2$ | $CH_3$ | $SO_2NHCH_3$ | H |
| $CH(NH_2)C_2H_5$ | H | H | H |
| $CH_3$ | CN | H | H |
| $CH_3$ | CN | $OCH_3$ | H |
| $CH_3$ | CN | Cl | H |
| $CH_2CONH_2$ | H | H | H |
| $CH_2CONH_2$ | H | Cl | H |
| $CH_2CONH_2$ | H | $OCH_3$ | H |
| $CH_2CONH_2$ | H | $CF_3$ | H |
| $CH_2CONH_2$ | H | $SO_2NH_2$ | H |
| $CH(CH_3)CONH_2$ | H | H | H |
| $CH_2OCOCH_3$ | $CH_3$ | H | H |
| $CH_2OCOCH_3$ | $CH_3$ | $CH_3$ | $CH_3$ |
| $C_6H_5$ | $C_2H_5$ | H | H |
| $C_6H_5$ | $C_2H_5$ | Cl | H |
| $CH_2CONH_2$ | $CH_3$ | F | H |
| $CH_2NHC_6H_5$ | $C_6H_5$ | H | H |
| $CH_2NHC_6H_5$ | $C_6H_5$ | $OCH_3$ | H |
| $CH_2NHC_6H_5$ | $C_6H_5$ | $SO_2N(CH_3)_2$ | H |
| $CH_2COOH$ | H | F | H |
| $CH_2COOH$ | H | Cl | H |
| $CH(OCH_3)_2$ | H | Cl | Cl |
| $CH(OCH_3)_2$ | H | $OCH_3$ | H |
| $CH(OCH_3)_2$ | H | $CF_3$ | H |
| $CH(OCH_3)_2$ | H | $SO_2NH_2$ | H |
| $CH(OC_2H_5)CH_3$ | $CH_3$ | H | H |
| $CH(OC_2H_5)CH_3$ | $CH_3$ | Cl | H |
| $CH_2CH_2COOCH_3$ | H | H | H |
| $CH_2CH_2COOCH_3$ | H | Cl | H |
| $CH_2CH_2COOCH_3$ | H | F | H |
| $CH_2CH_2COOCH_3$ | H | $CF_3$ | H |
| $CH_2CH_2COOCH_3$ | H | $OCH_3$ | H |
| $CH_2CH_2COOCH_3$ | H | $SO_2NHCH_3$ | H |
| $CH_2COOH$ | H | $CH_3$ | H |
| $CH_2CH_2COOCH_3$ | H | $SO_2NH_2$ | H |
| $CH_2OCH_3$ | H | $CH_3$ | $CH_3$ |
| $CH_2OCH_3$ | H | Cl | H |

-continued

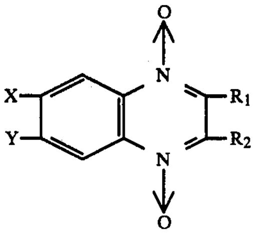

| $R_1$ | $R_2$ | X | Y |
|---|---|---|---|
| $CH_2CH_2OCH_3$ | H | $OCH_3$ | Cl |

In those reactions wherein an acyloxy group is present ($R_1$ or $R_2$), diisopropylamine or piperidine is used as base.

EXAMPLE LVII

The following compounds are prepared by the procedure of Example XIII-C from the appropriate β-keto ester

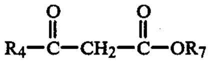

and benzofuroxan or a substituted benzofuroxan.

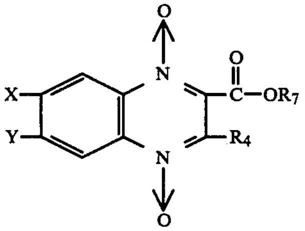

| X | Y | $R_7$ | $R_4$ |
|---|---|---|---|
| H | H | $C_2H_5$ | $CH_2OCOCH_3$* |
| Cl | H | $C_2H_5$ | $CH_2OCOCH_3$ |
| $CH_3$ | H | $C_2H_5$ | $CH_2OCOCH_3$* |
| $OCH_3$ | H | $C_2H_5$ | $CH_2OCOCH_3$ |
| $CF_3$ | H | $C_2H_5$ | $CH_2OCOCH_3$ |
| Cl | Cl | $C_2H_5$ | $CH_2OCOCH_3$ |
| H | H | $C_2H_5$ | $CH_2CN$*[(a)] |
| F | H | $C_2H_5$ | $CH_2CN$[(a)] |
| Cl | H | $C_2H_5$ | $CH_2CN$[(a)] |
| $CH_3$ | $CH_3$ | $C_2H_5$ | $CH_2CN$[(a)] |
| $SO_2NH_2$ | H | $C_2H_5$ | $CH_2CN$[(a)] |
| $OCH_3$ | H | $C_2H_5$ | $CH_2CN$[(a)] |
| H | H | $C_2H_5$ | $CH_2Cl$ |
| Cl | H | $C_2H_5$ | $CH_2Cl$ |
| $OCH_3$ | H | $C_2H_5$ | $CH_2Cl$ |
| H | H | $C_2H_5$ | $CH_2F$ |
| F | H | $C_2H_5$ | $CH_2F$ |
| $OCH_3$ | H | $C_2H_5$ | $CH_2F$ |
| $CF_3$ | H | $C_2H_5$ | $CH_2F$ |
| H | H | $C_2H_5$ | $CH_2SH$ |
| Cl | H | $C_2H_5$ | $CH_2SH$ |
| F | H | $C_2H_5$ | $CH_2SH$ |
| $OCH_3$ | H | $C_2H_5$ | $CH_2SH$ |
| $CH_3$ | H | $C_2H_5$ | $CH_2SH$ |
| $CH_3$ | $CH_3$ | $C_2H_5$ | $CH_2SH$ |
| H | H | $CH_3$ | $CH(OCH_3)_2$ |
| Cl | H | $CH_3$ | $CH(OCH_3)_2$ |
| Cl | Cl | $CH_3$ | $CH(OCH_3)_2$ |
| H | H | $C_2H_5$ | $CH_2SCH_3$ |
| $OCH_3$ | H | $C_2H_5$ | $CH_2SCH_3$ |
| $OC_2H_5$ | H | $C_2H_5$ | $CH_2SCH_3$ |
| Cl | H | $C_2H_5$ | $CH_2SCH_3$ |
| $CH_3$ | $CH_3$ | $C_2H_5$ | $CH_2SCH_3$ |

-continued

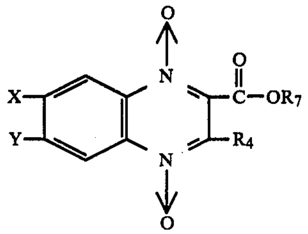

| X | Y | $R_7$ | $R_4$ |
|---|---|---|---|
| H | H | $C_2H_5$ | $CH_2NH_2$* |
| Cl | H | $C_2H_5$ | $CH_2NH_2$ |
| F | H | $C_2H_5$ | $CH_2NH_2$ |
| $OCH_3$ | H | $C_2H_5$ | $CH_2NH_2$ |
| $CF_3$ | H | $C_2H_5$ | $CH_2NH_2$ |
| $OCH_3$ | Cl | $C_2H_5$ | $CH_2NH_2$ |
| $CH_3$ | $CH_3$ | $C_2H_5$ | $CH_2NH_2$ |
| $SO_2NH_2$ | H | $C_2H_5$ | $CH_2NH_2$ |
| $SO_2N(CH_3)_2$ | H | $C_2H_5$ | $CH_2NH_2$ |
| $CF_3$ | H | $C_2H_5$ | $CH_2SH$ |
| $SO_2NH_2$ | H | $C_2H_5$ | $CH_2SH$ |
| $SO_2N(CH_3)_2$ | H | $C_2H_5$ | $CH_2SCH_3$ |
| H | H | $C_2H_5$ | $CH_2OCH_3$ |
| Cl | H | $C_2H_5$ | $CH_2OCH_3$ |
| F | H | $C_2H_5$ | $CH_2OCH_3$ |
| $SO_2N(CH_3)_2$ | H | $C_2H_5$ | $CH_2OCH_3$ |
| $OCH_3$ | H | $C_2H_5$ | $CH_2OCH_3$* |
| $CF_3$ | H | $C_2H_5$ | $CH_2OCH_3$ |
| H | H | $C_2H_5$ | $CH_2OC_2H_5$ |
| Cl | H | $C_2H_5$ | $CH_2OC_2H_5$ |
| F | H | $C_2H_5$ | $CH_2OC_2H_5$ |
| $OCH_3$ | H | $C_2H_5$ | $CH_2OC_2H_5$ |
| H | H | $C_2H_5$ | $CH_2OC_6H_5$* |
| Cl | H | $C_2H_5$ | $CH_2OC_6H_5$ |
| $CF_3$ | H | $C_2H_5$ | $CH_2OC_6H_5$ |
| $OCH_3$ | Cl | $C_2H_5$ | $CH_2OC_6H_5$ |
| $SO_2NH_2$ | H | $C_2H_5$ | $CH_2OC_6H_5$ |
| H | H | $CH_3$ | $CH_2OCH_3$ |
| Cl | H | $CH_3$ | $CH_2OCH_3$ |
| $OCH_3$ | H | $CH_3$ | $CH_2OCH_3$ |

*Sodium hydride is used as base in these reactions in place of sodium hydroxide.
[(a)]The corresponding 2-amino-3-carbethoxy compound is also formed.

EXAMPLE LVIII

The procedure of Example V is repeated but using the appropriate benzofuroxan and heterocyclic ketone

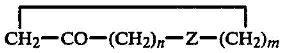

to give the following products:

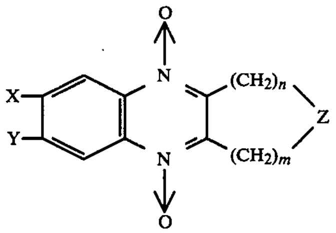

plus the isomers thereof wherein m=m+1 and n=n−1.

| X | Y | Z | m | n |
|---|---|---|---|---|
| H | H | NH | 0 | 2 |
| Cl | H | NH | 0 | 2 |
| F | H | NH | 0 | 2 |

-continued

| X | Y | Z | m | n |
|---|---|---|---|---|
| $OCH_3$ | H | NH | 0 | 2 |
| $CH_3$ | $CH_3$ | NH | 0 | 2 |
| $CF_3$ | H | NH | 0 | 2 |
| $SO_2NH_2$ | H | NH | 0 | 2 |
| $SO_2N(CH_3)_2$ | H | NH | 0 | 2 |
| H | H | $NCH_3$ | 0 | 2 |
| Cl | H | $NCH_3$ | 0 | 2 |
| $OCH_3$ | H | $NCH_3$ | 0 | 2 |
| Cl | Cl | $NCH_3$ | 0 | 2 |
| $CF_3$ | H | $NCH_3$ | 0 | 2 |
| $SO_2NH_2$ | H | $NCH_3$ | 0 | 2 |
| H | H | NH | 1 | 2 |
| Cl | H | NH | 1 | 2 |
| $OCH_3$ | H | NH | 1 | 2 |
| $CF_3$ | H | NH | 1 | 2 |
| $CH_3$ | $CH_3$ | NH | 1 | 2 |
| $SO_2NHCH_3$ | H | NH | 1 | 2 |
| H | H | $NCH_3$ | 1 | 2 |
| $CF_3$ | H | $NCH_3$ | 1 | 2 |
| Cl | H | $NCH_3$ | 1 | 2 |
| $OCH_3$ | Cl | $NCH_3$ | 1 | 2 |
| $SO_2N(CH_3)_2$ | H | $NCH_3$ | 1 | 2 |
| H | H | $NC_4H_9$ | 1 | 2 |
| Cl | H | $NC_4H_9$ | 1 | 2 |
| $OC_2H_5$ | H | $NC_4H_9$ | 1 | 2 |
| $CF_3$ | H | $NC_4H_9$ | 1 | 2 |
| H | H | $NC_6H_5$ | 1 | 2 |
| $OCH_3$ | Cl | $NC_6H_5$ | 1 | 2 |
| Cl | H | $NC_6H_5$ | 1 | 2 |
| Cl | H | $NC_7H_7$ | 1 | 2 |
| $CF_3$ | H | $NC_7H_7$ | 1 | 2 |
| H | H | NH | 1 | 3 |
| Cl | H | NH | 1 | 3 |
| $OCH_3$ | H | NH | 1 | 3 |
| $CH_3$ | H | NH | 1 | 3 |
| F | H | NH | 1 | 3 |
| $CF_3$ | H | NH | 1 | 3 |
| $SO_2NH_2$ | H | NH | 1 | 3 |
| $SO_2N(CH_3)_2$ | H | NH | 1 | 3 |
| H | H | O | 1 | 2 |
| Cl | H | O | 1 | 2 |
| F | H | O | 1 | 2 |
| $OCH_3$ | H | O | 1 | 2 |
| $CH_3$ | $CH_3$ | O | 1 | 2 |
| $CF_3$ | H | O | 1 | 2 |
| $SO_2NHCH_3$ | H | O | 1 | 2 |
| H | H | S | 1 | 2 |
| Cl | H | S | 1 | 2 |
| $OCH_3$ | H | S | 1 | 2 |
| $CF_3$ | H | S | 1 | 2 |
| F | H | S | 1 | 2 |
| $SO_2NH_2$ | H | S | 1 | 2 |
| $SO_2N(CH_3)_2$ | H | S | 1 | 2 |

EXAMPLE LIX

The following 2,3-polymethylenequinoxaline-di-N-oxides are prepared by the procedure of Example V from the appropriate benzofuroxan and cyclic ketone:

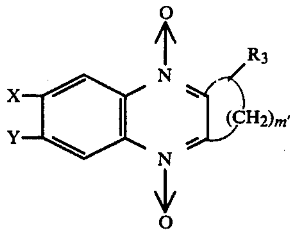

| 2,3-Polymethylene Moiety | X | Y |
|---|---|---|
| $-CH_2CH_2CH_2CH(COOH)-$ | H | H |
| $-CH_2CH_2CH(COOH)CH_2-$ | H | H |
| $-CH_2CH_2CH(COOH)CH_2-$ | Cl | H |
| $-CH_2CH(CH_3)CH(OH)-$ | H | H |

-continued

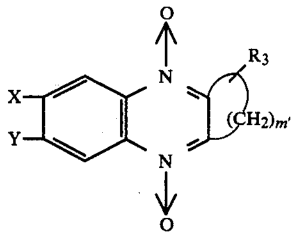

| 2,3-Polymethylene Moiety | X | Y |
|---|---|---|
| $-CH_2CH_2CH(COOCH_3)-$ | H | H |
| $-CH_2CH_2CH(COOCH_3)-$ | $OCH_3$ | H |
| $-CH_2CH_2CH_2CH(OH)-$ | H | H |
| $-CH_2CH(COOCH_3)CH_2-$ | H | H |
| $-CH_2CH(NH_2)CH_2-$ | H | H |
| $-CH_2CH_2CH(NH_2)-$ | H | H |
| $-CH_2CH_2CH_2CH(COOH)-$ | F | H |
| $-CH_2CH_2CH_2CH(COOH)-$ | Cl | Cl |
| $-CH_2CH_2CH(COOH)CH_2-$ | $CH_3$ | H |
| $-CH_2CH(CH_3)CH(OH)-$ | Cl | H |
| $-CH_2CH_2CH(COOCH_3)-$ | $OC_2H_5$ | H |
| $-CH_2CH(COOCH_3)CH_2-$ | $OCH_3$ | Cl |
| $-CH_2CH(NH_2)CH_2-$ | $OCH_3$ | H |
| $-CH_2CH(NH_2)CH_2-$ | Cl | H |
| $-CH_2CH(NH_2)CH_2-$ | $CF_3$ | H |
| $-CH_2CH(NH_2)CH_2-$ | $SO_2N(CH_3)_2$ | H |
| $-CH_2CH(COOCH_3)CH_2-$ | $CF_3$ | H |
| $-CH_2CH_2CH_2CH(OH)-$ | $CF_3$ | H |
| $-CH_2CH_2CH_2CH(OH)-$ | $SO_2NH_2$ | H |
| $-CH_2CH_2CH(Cl)-$ | H | H |
| $-CH_2CH_2CH(Cl)-$ | Cl | H |
| $-CH_2CH_2CH(Cl)-$ | $CF_3$ | H |
| $-CH_2CH_2CH(Cl)-$ | $OCH_3$ | H |
| $-CH_2CH_2CH(Cl)-$ | $SO_2NH_2$ | H |
| $-CH_2CH_2CH(Cl)-$ | $CH_3$ | $CH_3$ |
| $-CH_2CH_2CH(Br)-$ | H | H |
| $-CH_2CH_2CH_2CH(Cl)-$ | H | H |
| $-CH_2CH_2CH_2CH(Cl)-$ | Cl | H |
| $-CH_2CH_2CH_2CH(Cl)-$ | $OCH_3$ | Cl |
| $-CH_2CH_2CH_2CH(Cl)-$ | $SO_2N(CH_3)_2$ | H |
| $-CH_2CH(CH_3)CH(OCH_3)-$ | H | H |
| $-CH_2CH(CH_3)CH(OCH_3)-$ | Cl | H |
| $-CH_2CH_2CH_2CH(OCH_3)-$ | H | H |
| $-CH_2CH_2CH_2CH(OCH_3)-$ | $OCH_3$ | H |
| $-CH_2CH_2CH_2CH(OCH_3)-$ | F | H |
| $-CH_2CH_2CH_2CH(OCH_3)-$ | $SO_2NHCH_3$ | H |
| $-CH_2CH_2CH(COCH_3)-$ | H | H |
| $-CH_2CH_2CH(COCH_3)-$ | Cl | H |
| $-CH_2CH_2CH(COCH_3)-$ | $OCH_3$ | H |
| $-CH(CH_3)CH_2CH_2CH(OH)-$ | H | H |
| $-CH(CH_3)CH_2CH_2CH(OH)-$ | $OCH_3$ | H |
| $-CH(CH_3)CH_2CH_2CH(OH)-$ | $OCH_3$ | Cl |
| $-CH(CH_3)CH_2CH_2CH(Cl)-$ | H | H |
| $-CH_2CH(CH_3)CH(OCOCH_3)-$ | H | H |
| $-CH_2CH(CH_3)CH(OCOCH_3)-$ | Cl | H |
| $-CH_2CH(CH_3)CH(OCOCH_3)-$ | $OCH_3$ | H |
| $-CH_2CH_2CH_2CH(OCOCH_3)-$ | H | H |
| $-CH_2CH_2CH_2CH(OCOCH_3)-$ | $CF_3$ | H |
| $-CH_2CH_2CH_2CH(OCOCH_3)-$ | $SO_2N(CH_3)_2$ | H |

EXAMPLE LX

Repetition of the procedure of Example XII but using the appropriate $\beta$-diketone ($R_5COCH_2COR_4$) in place of acetylacetone and the appropriate benzofuroxan reactant produces the following compounds:

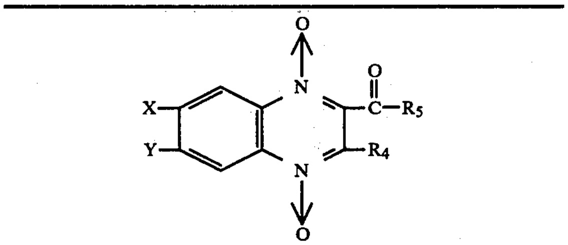

| R5 | R4 | X | Y |
|---|---|---|---|
| $C_6H_5$ | $CH_3$ | H | H |
| $C_6H_5$ | $CH_3$ | Cl | H |
| $C_6H_5$ | $CH_3$ | $OCH_3$ | H |
| $C_6H_5$ | $CH_3$ | F | H |
| $C_6H_5$ | $CH_3$ | $CF_3$ | H |
| $C_6H_5$ | $CH_3$ | $SO_2NHCH_3$ | H |
| $C_6H_5$ | $C_2H_5$ | H | H |
| $C_6H_5$ | i-$C_3H_7$ | H | H |
| $COC(CH_3)_3$ | $C_6H_5$ | H | H |
| $COCH(CH_3)_2$ | $C_6H_5$ | H | H |
| $CH_3$ | p-tolyl | H | H |
| $CH_3$ | p-tolyl | Cl | H |
| $CH_3$ | p-tolyl | $OCH_3$ | H |
| $CH_3$ | $4(CH_3O)C_6H_4$ | H | H |
| $CH_3$ | $4(CH_3O)C_6H_4$ | F | H |
| $CH_3$ | $4(CH_3O)C_6H_4$ | $CF_3$ | H |
| $CH_3$ | $4(CH_3O)C_6H_4$ | $SO_2NH_2$ | H |
| $CH_3$ | $4(Br)C_6H_4$ | H | H |
| $CH_3$ | $4(NO_2)C_6H_4$ | H | H |
| $CH_3$ | $4(NO_2)C_6H_4$ | Cl | H |
| $C_6H_{13}$ | $C_6H_{13}$ | H | H |
| $C_6H_{13}$ | $C_6H_{13}$ | Cl | H |
| $C_6H_{13}$ | $C_6H_{13}$ | $CF_3$ | H |
| $C_6H_{13}$ | $C_6H_{13}$ | $OCH_3$ | Cl |
| $C_6H_{13}$ | $C_6H_{13}$ | $SO_2NHCH_3$ | H |
| $CH_3$ | $CH_3$ | $SO_2NH_2$ | H |
| $C_6H_5$ | $C_6H_5$ | Cl | H |
| $C_6H_5$ | $C_6H_5$ | F | H |
| $C_6H_5$ | $C_6H_5$ | $OCH_3$ | H |
| $C_6H_5$ | $C_6H_5$ | $SO_2N(CH_3)$ | H |
| $C_2H_5$ | $C_2H_5$ | Cl | H |
| $C_2H_5$ | $C_2H_5$ | Cl | Cl |
| $C_2H_5$ | $C_2H_5$ | $SO_2NHCH_3$ | H |
| $C_2H_5$ | $C_2H_5$ | $CF_3$ | H |
| $C_2H_5$ | $C_2H_5$ | $OC_2H_5$ | H |

EXAMPLE LXI

Repetition of the procedure of Example XXXVI but using the appropriate benzofuroxan and malonate in place of benzofuroxan and dimethylmalonate produces the following compounds along with the reduced form thereof.

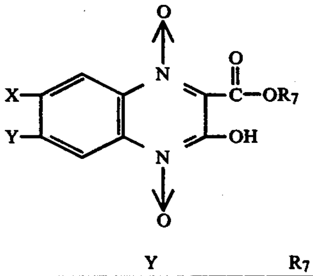

| X | Y | R7 |
|---|---|---|
| H | H | $C_6H_5$ |
| Cl | H | $C_6H_5$ |
| $OCH_3$ | H | $C_6H_5$ |
| $CH_3$ | H | $CH_3$ |
| $OC_2H_5$ | H | $C_2H_5$ |
| $CF_3$ | H | $C_6H_5$ |
| Cl | $OCH_3$ | $CH_3$ |

-continued

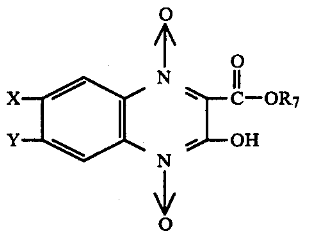

| X | Y | R7 |
|---|---|---|
| F | H | $CH_3$* |
| $CF_3$ | H | $CH_3$ |
| $SO_2N(CH_3)_2$ | H | $CH_3$ |
| $CH_3$ | $CH_3$ | n-$C_4H_9$ |
| Cl | H | $C_4H_9$ |
| F | H | n-$C_4H_9$ |
| $SO_2NH_2$ | H | $CH_3$ |
| $SO_2NH_2$ | H | n-$C_4H_9$ |
| H | H | $C_7H_7$* |
| Cl | H | $C_7H_7$ |
| $OCH_3$ | H | $C_7H_7$ |
| $SO_2NHCH_3$ | H | $C_7H_7$ |

*Sodium hydride used as base in place of sodium methoxide.

EXAMPLE LXII

The substitution of a malonamate that is a half-ester, half-amide of malonic acid for dimethylmalonate produces the following quinoxalines when reacted with the appropriate benzofuroxan according to the procedure of Example XXXVI:

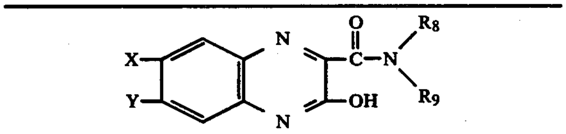

| X | Y | R8 | R9 |
|---|---|---|---|
| H | H | H | H |
| Cl | H | H | H |
| F | H | H | H |
| $OCH_3$ | H | H | H |
| $CF_3$ | H | H | H |
| $CH_3$ | $CH_3$ | H | H |
| $SO_2N(CH_3)_2$ | H | H | H |
| Br | H | $CH_3$ | H |
| Cl | H | $CH_3$ | H |
| $OCH_3$ | H | $CH_3$ | H |
| $SO_2NH_2$ | H | $CH_3$ | H |
| H | H | $CH_3$ | $CH_3$ |
| $CF_3$ | H | $CH_3$ | $CH_3$ |
| Cl | H | $CH_3$ | $CH_3$ |
| $OCH_3$ | Cl | $CH_3$ | $CH_3$ |
| $SO_2NHCH_3$ | H | $CH_3$ | $CH_3$ |
| H | H | $C_2H_5$ | H |
| F | H | $C_2H_5$ | H |
| $OCH_3$ | H | $C_2H_5$ | H |
| $SO_2NH_2$ | H | $C_2H_5$ | H |
| H | H | i-$C_3H_7$ | H |
| H | H | n-$C_4H_9$ | H |
| Cl | H | n-$C_4H_9$ | H |
| H | H | $C_6H_5$ | H |
| Cl | H | $C_6H_5$ | H |
| $OCH_3$ | H | $C_6H_5$ | H |
| $SO_2N(CH_3)_2$ | H | $C_6H_5$ | H |
| H | H | $C_6H_5$ | $CH_3$ |
| Cl | H | $C_6H_5$ | $CH_3$ |
| H | H | $C_7H_7$ | H |
| $OCH_3$ | H | $C_7H_7$ | H |
| Br | H | $C_7H_7$ | $CH_3$ |
| $CF_3$ | H | $C_6H_5$ | H |
| $SO_2NHCH_3$ | H | $C_6H_5$ | H |
| $OCH_3$ | Cl | $C_6H_5$ | H |

-continued

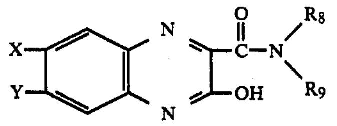

| X | Y | $R_8$ | $R_9$ |
|---|---|---|---|
| Cl | Cl | $C_2H_5$ | $C_2H_5$ |
| $OC_2H_5$ | H | $CH_3$ | H |
| $CF_3$ | H | $C_2H_5$ | $C_2H_5$ |
| $CF_3$ | H | $C_7H_7$ | H |
| $SO_2NH_2$ | H | $C_7H_7$ | H |

The quinoxalines thus prepared are oxidized by known methods to the corresponding di-N-oxides. A favored method comprises treating the quinoxaline in chloroform with an equimolar amount of m-chloroperbenzoic acid at room temperature for a period of three days. The precipitated m-chlorobenzoic acid is filtered off and the chloroform solution washed with saturated aqueous sodium bicarbonate. The chloroform solution is dried ($Na_2SO_4$) and taken to dryness under reduced pressure to give the product.

EXAMPLE LXIII

Repetition of the procedure of Example XXVI but using the appropriate substituted benzofuroxan in place of benzofuroxan provides the following compounds:

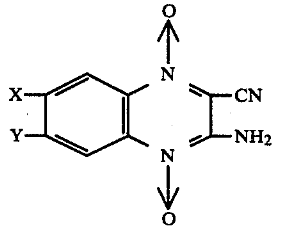

| X | Y |
|---|---|
| $CH_3$ | H |
| Cl | H |
| F | H |
| $SO_2NH_2$ | H |
| $SO_2N(CH_3)_2$ | H |
| $CF_3$ | H |
| Br | H |
| $OC_2H_5$ | H |
| $CH_3$ | $CH_3$ |
| $OCH_3$ | Cl |
| $SO_2NHCH_3$ | H |
| Cl | Cl |

EXAMPLE LXIV

2-Carbomethoxy-3-Aminoquinoxaline-di-N-Oxide

A mixture of methyl cyanoacetate (0.3 mole), benzofuroxan (0.25 mole), triethylamine (10 ml.) and tetrahydrofuran (200 ml.) is stirred at room temperature for one hour then allowed to stand overnight. The product which precipitates is filtered and dried.

In like manner the following compounds are prepared from the appropriate reactants:

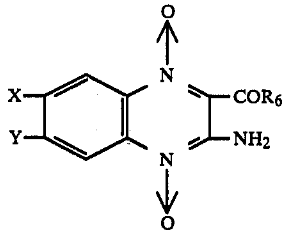

| X | Y | $R_6$ | X | Y | $R_6$ |
|---|---|---|---|---|---|
| H | H | $OC_2H_5$ | H | H | $NH_2$ |
| H | H | $O(n-C_4H_9)$ | H | H | $N(CH_3)_2$ |
| H | H | $OC_6H_5$ | H | H | $NHC_6H_5$ |
| H | H | $OC_7H_7$ | F | H | $N(CH_3)_2$ |
| $CH_3$ | H | $OCH_3$ | $SO_2NH_2$ | H | $NH_2$ |
| Cl | Cl | $OCH_3$ | $CF_3$ | H | $NH_2$ |
| Cl | H | $OCH_3$ | $CH_3$ | H | $NHC_2H_5$ |
| F | H | $OCH_3$ | Cl | H | $NH_2$ |
| $SO_2NH_2$ | H | $OCH_3$ | $OCH_3$ | H | $NH_2$ |
| $SO_2N(CH_3)_2$ | H | $OCH_3$ | $OC_2H_5$ | H | $NH_2$ |
| $CF_3$ | H | $OCH_3$ | $CH_3$ | $CH_3$ | $NH_2$ |
| $OC_2H_5$ | H | $OCH_3$ | $OCH_3$ | H | $N(CH_3)_2$ |
| $OCH_3$ | Cl | $OCH_3$ | Cl | H | $N(C_2H_5)_2$ |
| Cl | H | $OC_6H_5$ | $SO_2N(CH_3)_2$ | H | $N(CH_3)_2$ |
| $OCH_3$ | H | $OC_6H_5$ | $SO_2NH_2$ | H | $N(C_2H_5)_2$ |
| Cl | H | $NHC_6H_5$ | $OCH_3$ | H | $N(C_6H_5)_2$ |

EXAMPLE LXV

The following 3-hydroxy-2-quinoxalinecarboxamides are prepared from the appropriate malonic acid diamide (B—CO—$CH_2$—CO—B') and benzofuroxan by the procedure of Example XXXVI:

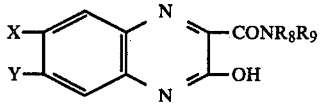

| X | Y | B | B' | $R_8$ | $R_9$ |
|---|---|---|---|---|---|
| H | H | $NH_2$ | $NH_2$ | H | H |
| Cl | H | $NH_2$ | $NH_2$ | H | H |
| H | H | $HNCH_3$ | $HNCH_3$ | H | $CH_3$ |
| Cl | H | $HNCH_3$ | $HNCH_3$ | H | $CH_3$ |
| $OCH_3$ | H | $HNCH_3$ | $HNCH_3$ | H | $CH_3$ |
| H | H | $HNC_6H_5$ | $HNC_6H_5$ | H | $C_6H_5$ |
| F | H | $HNC_6H_5$ | $HNC_6H_5$ | H | $C_6H_5$ |
| $CF_3$ | H | $HNC_6H_5$ | $HNC_6H_5$ | H | $C_6H_5$ |
| $SO_2NH_2$ | H | $HNC_6H_5$ | $HNC_6H_5$ | H | $C_6H_5$ |
| H | H | $NH_2$ | $HNC_6H_5$ | H | $C_6H_5$ |

Oxidation of these quinoxalines by the procedure set forth in Example LXII produces the corresponding di-N-oxides.

EXAMPLE LXVI

The procedure of Example IX-A is repeated using the appropriate benzofuroxan and substituting a ketosulfonic acid of the formula $R_4$—CO—$(CH_2)_m$—$SO_3H$ for 4-hydroxy-2-butanone to give:

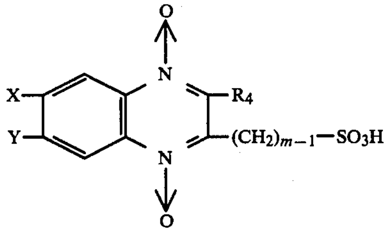

| X | Y | m−1 | $R_4$ |
|---|---|---|---|
| H | H | 0 | $CH_3$ |
| Cl | H | 0 | $CH_3$ |
| $OCH_3$ | H | 0 | $CH_3$ |
| $SO_2NH_2$ | H | 0 | $CH_3$ |
| H | H | 1 | $CH_3$ |
| Cl | H | 1 | $CH_3$ |
| F | H | 1 | $CH_3$ |
| $SO_3N(CH_3)_2$ | H | 1 | $CH_3$ |
| H | H | 1 | $C_6H_5$ |
| F | H | 1 | $C_6H_5$ |
| $OCH_3$ | H | 1 | $C_6H_5$ |
| $SO_2NHCH_3$ | H | 1 | $C_6H_5$ |
| $CF_3$ | H | 0 | $CH_3$ |
| $CF_3$ | H | 1 | $CH_3$ |

EXAMPLE LXVII

2-Formylquinoxaline-di-N-Oxide Diacetals

Pyruvaldehyde dimethylacetal (26.0 g., 0.22 mole), benzofuroxan (27.2 g., 0.2 mole) and N,N-dimethylformamide (60 ml.) are placed in a three-necked round-bottomed flask and cooled to 0°-5° C. Ammonia (anhydrous) gas is passed through the stirred solution for thirty minutes at the end of which time the ammonia inlet tube is removed and replaced with a drying tube and the ammonia outlet tube replaced with a glass stopper. The reaction mixture is then allowed to stand at room temperature for five days. The product is filtered off, slurried in ether, filtered and dried: M.P. 144°-146.5° C., 72.3 percent yield.

In like manner the following compounds are prepared:

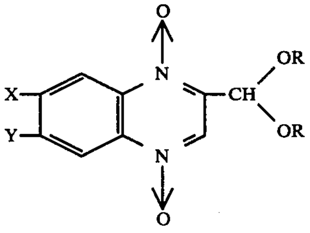

| X | Y | R | X | Y | R |
|---|---|---|---|---|---|
| H | H | $C_2H_5$ | $OCH_3$ | H | $CH_3$ |
| H | H | i-$C_3H_7$ | $SO_2NH_2$ | H | $CH_3$ |
| H | H | n-$C_4H_9$ | $CH_3$ | H | n-$C_4H_9$ |
| Cl | H | $CH_3$ | $SO_2N(CH_3)_2$ | H | n-$C_4H_9$ |
| F | H | $CH_3$ | Cl | H | n-$C_4H_9$ |
| $CH_3$ | Cl | $C_2H_5$ | $CF_3$ | H | $CH_3$ |

EXAMPLE LXVIII

The procedure of Example XLVI is repeated to provide the following 2-carbalkoxy-3-formylquinoxaline-di-N-oxide diacetals:

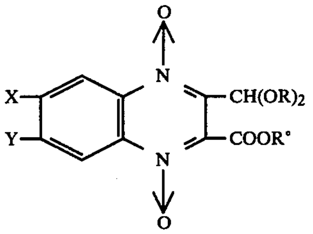

| X | Y | R | R° |
|---|---|---|---|
| Cl | H | $C_2H_5$ | $C_2H_5$ |
| F | H | $C_2H_5$ | $C_2H_5$ |
| $OCH_3$ | H | $C_2H_5$ | $C_2H_5$ |
| $CH_3$ | H | $C_2H_5$ | $C_2H_5$ |
| $CF_3$ | H | $C_2H_5$ | $C_2H_5$ |
| $SO_2NH_2$ | H | $C_2H_5$ | $C_2H_5$ |
| H | H | $CH_3$ | $C_2H_5$ |
| Cl | H | $CH_3$ | $C_2H_5$ |
| $OCH_3$ | H | $CH_3$ | $C_2H_5$ |
| H | H | $CH_3$ | $CH_3$ |
| H | H | $C_4H_9$ | $C_4H_9$ |
| Cl | H | $C_4H_9$ | $C_4H_9$ |
| $CH_3$ | H | $C_4H_9$ | $C_4H_9$ |
| H | H | $C_4H_9$ | $C_2H_5$ |
| $SO_2N(CH_3)_2$ | H | $C_4H_9$ | $C_2H_5$ |
| $SO_2NH(CH_3)$ | H | $C_4H_9$ | $C_2H_5$ |

The necessary alkyl γ,γ-dialkoxyacetoacetates are prepared according to the procedure described by Johnson and Cretcher, J. Am. Chem. Soc. 37, 2147-9 (1915) which comprises reacting the appropriate alkyldialkoxyacetate with sodium and an alkyl acetate. The procedure is exemplified below in the preparation of methyl γ,γ-dimethoxyacetoacetate.

Sodium (56.2 g.) is dissolved in absolute ethanol (800 ml.) and the solution heated to 80° C. on a water bath. Dichloroacetic acid (105 g.) is then slowly added via a dropping funnel. The mixture is then cooled to 10° C., hydrochloric acid (35 ml.) in absolute ethanol (50 ml.) is added and the solution allowed to stand at room temperature for eighteen hours. The hydrochloric acid is then neutralized by adding the stoichiometric amount of sodium ethylate in ethanol solution. The alcohol is removed by distillation under reduced pressure and the residue diluted by addition of cold water (20 ml.). The aqueous solution is extracted with ether (3×250 ml.), the ethereal solution dried and, after removal of the ether, distilled in vacuo to give ethyldiethoxyacetate.

Ethyldiethoxyacetate (32 g.) and methylacetate (25 g.) are placed in a flask equipped with stirrer and reflux condenser and heated to reflux. Metallic sodium wire (6.5 g.) is introduced into the flask in small portions and heating continued until the sodium is completely dissolved. Methylacetate (25 g.) and metallic sodium wire (6.5 g.) are then added and heating continued until the solution is clear. The mixture is cooled, a large volume of ice water cautiously added and the mixture extracted with ether. The aqueous solution is acidified with hydrochloric acid at 10° C. to 15° C. and the desired product extracted with ether. The ethereal extract is dried ($Na_2SO_4$), the ether removed and the residue distilled in vacuo to give methyl γ,γ-diethoxyacetoacetate.

EXAMPLE LXIX

Repetition of the procedures of Examples XVII through XXII but using the appropriate benzofuroxan produces the following 1-hydroxybenzimidazole-3-oxides:

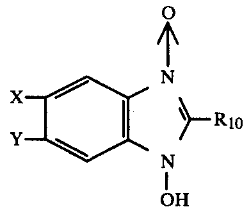

| X | $R_{10}$ |
|---|---|
| Cl | H |
| F | H |
| $OCH_3$ | H |
| $CH_3$ | H |
| $CF_3$ | H |
| $SO_2NH_2$ | H |
| Cl | $CH_3$ |
| F | $CH_3$ |
| $OCH_3$ | $CH_3$ |
| $SO_2NHCH_3$ | $CH_3$ |
| Cl | $C_2H_5$ |
| $OCH_3$ | n-$C_3H_7$ |
| F | $CH_2CH_2CONH_2$ |
| $OCH_3$ | $CH_2CH_2CONH_2$ |
| $SO_2N(CH_3)_2$ | $CH_2CH_2CONH_2$ |
| $CF_3$ | $CH_2CH_2CONH_2$ |
| Cl | $COOC_2H_5$ |
| F | $COOC_2H_5$ |
| $OCH_3$ | $COOC_2H_5$ |

EXAMPLE LXX

The following 2H-benzimidazole-1,3-dioxides are prepared by the procedures of Examples XXIII through XXV but using the appropriate benzofuroxan and nitro compounds as reactants:

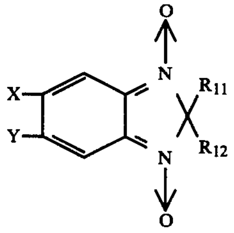

| X | $R_{11}$ | $R_{12}$ | X | $R_{11}$ | $R_{12}$ |
|---|---|---|---|---|---|
| Cl | $CH_3$ | $CH_3$ | H | $CH_3$ | $CH_2Br$ |
| F | $CH_3$ | $CH_3$ | F | $CH_3$ | $CH_2Br$ |
| $OCH_3$ | $CH_3$ | $CH_3$ | $OCH_3$ | $CH_3$ | $CH_2Br$ |
| $CF_3$ | $CH_3$ | $CH_3$ | H | $CH_3$ | $CH_2OH$ |
| $SO_2N(CH_3)_2$ | $CH_3$ | $CH_3$ | Cl | $CH_3$ | $CH_2OH$ |
| Cl | $CH_3$ | $C_2H_5$ | $OCH_3$ | $CH_3$ | $CH_2OH$ |
| $OCH_3$ | $CH_3$ | $C_2H_5$ | $SO_2N(CH_3)_2$ | $CH_3$ | $CH_2OH$ |
| $CH_3$ | $CH_3$ | $C_2H_5$ | H | $C_2H_5$ | $CH_2N(C_2H_5)_2$ |
| $SO_2NH_2$ | $CH_3$ | $C_2H_5$ | $OCH_3$ | $C_2H_5$ | $CH_2N(C_2H_5)_2$ |
| Cl | $-CH_2CH_2CH_2CH_2CH_2-$ | | F | $C_2H_5$ | $CH_2N(C_2H_5)_2$ |
| $OCH_3$ | $-CH_2CH_2CH_2CH_2CH_2-$ | | $SO_2NH_2$ | $C_2H_5$ | $CH_2N(C_2H_5)_2$ |
| F | $-CH_2CH_2CH_2CH_2CH_2-$ | | | | |
| $SO_2NH_2$ | $-CH_2CH_2CH_2CH_2CH_2-$ | | | | |
| H | $CH_3$ | $CH_2Cl$ | | | |
| Cl | $CH_3$ | $CH_2Cl$ | | | |
| $OCH_3$ | $CH_3$ | $CH_2Cl$ | | | |
| $CH_3$ | $CH_3$ | $CH_2Cl$ | | | |
| $SO_2NHCH_3$ | $CH_3$ | $CH_2Cl$ | | | |
| $CF_3$ | $CH_3$ | $CH_2Cl$ | | | |

What is claimed is:

1. A compound of the formula:

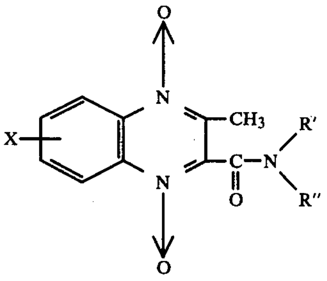

wherein X is trifluoromethyl, sulfonamide, N-methylsulfonamide and N,N-dimethylsulfonamide; and each of R' and R'' is selected from the group consisting of hydrogen and lower alkyl.

2. A compound of the formula

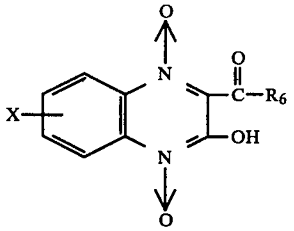

wherein $R_6$ is selected from the group consisting of lower alkoxy, aryloxy, benzyloxy and $NR_8R_9$ wherein each of $R_8$ and $R_9$ is selected from the group consisting of hydrogen, lower alkyl and phenyl; and X is selected from the group consisting of hydrogen, chloro, fluoro, methyl, methoxy, trifluoromethyl, sulfonamido, N-methylsulfonamido and N,N-dimethylsulfonamido.

3. A compound of the formula

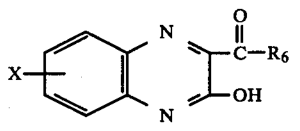

wherein $R_6$ is selected from the group consisting of lower alkoxy, aryloxy, benzyloxy and $NR_8R_9$ wherein each of $R_8$ and $R_9$ is selected from the group consisting of hydrogen, lower alkyl and phenyl; and X is selected from the group consisting of hydrogen, chloro, fluoro, methyl, methoxy, trifluoromethyl, sulfonamido, N-methylsulfonamido and N,N-dimethylsulfonamido.

4. A compound of the formula

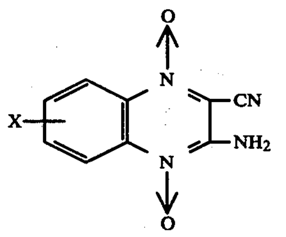

wherein X is selected from the group consisting of hydrogen, chloro, fluoro, methyl, methoxy, trifluoromethyl, sulfonamido, N-methylsulfonamido and N,N-dimethylsulfonamido.

5. 2-Cyano-3-aminoquinoxaline-di-N-oxide, a compound according to claim 4 wherein X is hydrogen.

6. 2-Cyano-3-amino-6(or 7)-chloroquinoxaline-di-N-oxide, a compound according to claim 4 wherein X is 6(or 7)-chloro.

7. 2-Cyano-3-amino-6(or 7)-fluoroquinoxaline-di-N-oxide, a compound according to claim 4 wherein X is 6(or 7)-fluoro.

8. A compound of the formula

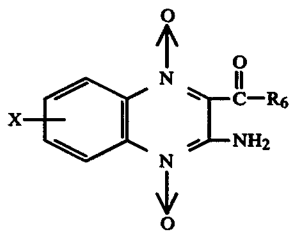

wherein X is selected from the group consisting of hydrogen, chloro, fluoro, methyl, methoxy, trifluoromethyl, sulfonamido, N-methylsulfonamido and N,N-dimethylsulfonamido; and $R_6$ is selected from the group consisting of lower alkoxy, benzoyloxy, aryloxy, and $NR_8R_9$ wherein each of $R_8$ and $R_9$ is selected from the group consisting of hydrogen, lower alkyl and phenyl.

9. A compound of the formula

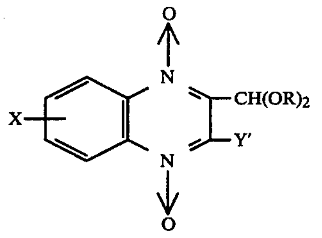

wherein R is lower alkyl; X is selected from the group consisting of hydrogen, chloro, fluoro, methyl, methoxy, trifluoromethyl, sulfonamido, N-methylsulfonamido and N,N-dimethylsulfonamido; and Y' is selected from the group consisting of hydrogen, carbo(-lower alkoxy) and lower alkyl.

10. 2-Formylquinoxaline-di-N-oxide dimethylacetal, a compound according to claim 9 wherein R is methyl and each of X and Y' is hydrogen.

11. 2-Carbethoxy-3-formylquinoxaline-di-N-oxide diethylacetal, a compound according to claim 9 wherein R is ethyl, X is hydrogen and Y' is carbethoxy.

12. A compound of the formula

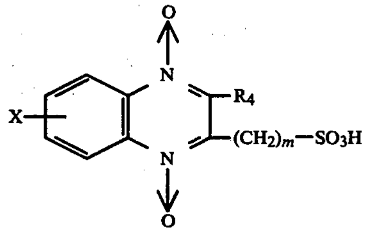

wherein X is selected from the group consisting of hydrogen, chloro, fluoro, methyl, methoxy, trifluoromethyl, sulfonamido, N-methylsulfonamido and N,N-dimethylsulfonamido; $R_4$ is selected from the group consisting of lower alkyl and phenyl; and m is an integer from 0 to 1.

13. A compound of the formula

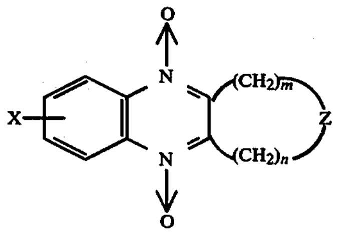

wherein X is selected from the group consisting of hydrogen, chloro, fluoro, methyl, methoxy, trifluoromethyl, sulfonamido, N-methylsulfonamido and N,N-dimethylsulfonamido; Z is selected from the group consisting of oxygen, sulfur, imino and N-methylimino; m is an integer from 0 to 1 and n is an integer from 2 to 3.

14. A compound of the formula

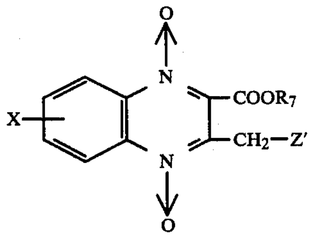

wherein X is selected from the group consisting of hydrogen, chloro, fluoro, methyl, methoxy, trifluoromethyl, sulfonamido, N-methylsulfonamido and N,N-dimethylsulfonamido; $R_7$ is lower alkyl; and Z' is selected from the group consisting of halogen, lower alkoxy, lower alkanoyloxy, cyano, amino, mercapto and lower alkylmercapto.

15. 2-amino-3-cyano-di-N-oxide of the formula:

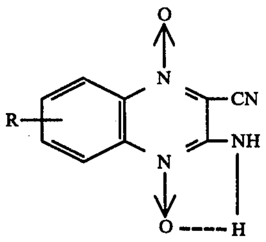

in which R is hydrogen, halogen, lower alkyl or lower alkoxy.

16. N,N-dimethyl-3-methyl-7-N-methylsulfonamido-2-quinoxalinecarboxamide-di-N-oxide, a compound according to claim 1 wherein X is 7-N-methylsulfonamido, R' is methyl and R'' is methyl.

17. N,N-dimethyl-3-methyl-7-N,N-dimethylsulfonamido-2-quinoxalinecarboxamide-di-N-oxide, a compound according to claim 1 wherein X is 7-N,N-dimethylsulfonamido, R' is methyl and R'' is methyl.

* * * * *

UNITED STATES PATENT AND TRADEMARK OFFICE

CERTIFICATE OF CORRECTION

PATENT NO. : 4,343,942

DATED : August 10, 1982

INVENTOR(S) : Costas H. Issidorides et al.

It is certified that error appears in the above-identified patent and that said Letters Patent is hereby corrected as shown below:

Column 6, lines 25 to 30, the portion of formula IVB, should appear as shown below:

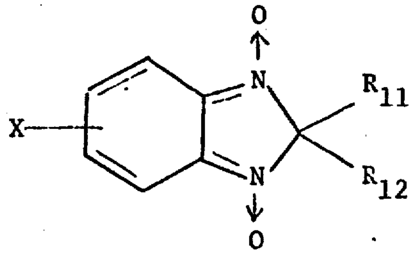

Signed and Sealed this

*Twelfth* Day of *October 1982*

[SEAL]

*Attest:*

GERALD J. MOSSINGHOFF

*Attesting Officer* *Commissioner of Patents and Trademarks*